US012245576B2

(12) United States Patent
Atkinson et al.

(10) Patent No.: US 12,245,576 B2
(45) Date of Patent: Mar. 11, 2025

(54) METHOD FOR GENETIC MANIPULATION OF SAP-FEEDING INSECTS

(71) Applicant: The Regents of the University of California, Oakland, CA (US)

(72) Inventors: Peter W. Atkinson, Riverside, CA (US); Linda L. Walling, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 1189 days.

(21) Appl. No.: 16/960,285

(22) PCT Filed: Jan. 9, 2019

(86) PCT No.: PCT/US2019/012939
§ 371 (c)(1),
(2) Date: Jul. 6, 2020

(87) PCT Pub. No.: WO2019/140010
PCT Pub. Date: Jul. 18, 2019

(65) Prior Publication Data
US 2021/0105986 A1  Apr. 15, 2021

Related U.S. Application Data

(60) Provisional application No. 62/734,953, filed on Sep. 21, 2018, provisional application No. 62/615,826, filed on Jan. 10, 2018.

(51) Int. Cl.
*A01K 67/033* (2006.01)
*G01N 33/50* (2006.01)

(52) U.S. Cl.
CPC ..... *A01K 67/0339* (2013.01); *G01N 33/5085* (2013.01); *A01K 2217/07* (2013.01); *A01K 2227/706* (2013.01); *A01K 2267/03* (2013.01)

(58) Field of Classification Search
CPC .................. A01K 67/0339; A01K 2227/706
See application file for complete search history.

(56) References Cited

U.S. PATENT DOCUMENTS

| 5,113,799 | A | 5/1992 | Carr et al. |
| 5,986,181 | A | 11/1999 | Trolinder et al. |
| 9,271,503 | B2 | 3/2016 | Mensah |
| 2014/0033367 | A1 | 1/2014 | Daniell |

FOREIGN PATENT DOCUMENTS

| CA | 1341167 | * | 1/2001 | ............... C12N 5/10 |

OTHER PUBLICATIONS

Kuo (In vitro Cell Dev Biol-Plant, 41:453-456, 2005).*
Flores , "Possible New Control for Whiteflies Discovered", United States Department of Agriculture, Available Online at URL: <https://www.ars.usda.gov/news-events/news/researchnews/ 2007/possible-new-control-for-whiteflies-discovered/>; May 11, 2007.
Gamborg et al., "Nutrient Requirements of Suspension Cultures of Soybean Root Cells", Experimental Cell Research, vol. 50, No. 1, Apr. 1968, pp. 151-158.
PCT/US2019/012939 , "International Search Report and Written Opinion", May 14, 2019, 11 pages.
Prusty et al., "The Plant Hormone Indoleacetic Acid Induces Invasive Growth in *Saccharomyces cerevisiae*", PNAS, vol. 101, No. 12, Mar. 23, 2004, pp. 4153-4157.
Teixeira Da Silva et al., "Disinfection Procedures for in Vitro Propagation of Anthurium", Folia Horticulturae, vol. 27, No. 1, 2015, pp. 3-14.

* cited by examiner

*Primary Examiner* — Valarie E Bertoglio
(74) *Attorney, Agent, or Firm* — Kilpatrick Townsend & Stockton LLP

(57) ABSTRACT

The invention provides methods for rearing and genetic manipulation of the genome of sap-feeding insects (e.g., whiteflies and others) to identify genetic targets for pest control, insecticides for pest control, and approaches to the genetic control of these pests.

5 Claims, 20 Drawing Sheets

560 plates (colonies) per incubator 3920 plates per 100 sq ft room vs 1 plant (colony) per bugdorm (4 sq ft)

3,920 plants = 15,680 sq ft
11 high-level containment greenhouses
($$$)

**Injecting Eggs *In situ*.**

Males and females added to plate → Females deposit eggs → ~50% → → ~40% → WT / mutants

Current efficiency
1 mutant/100 injections
5 mutants/day per person

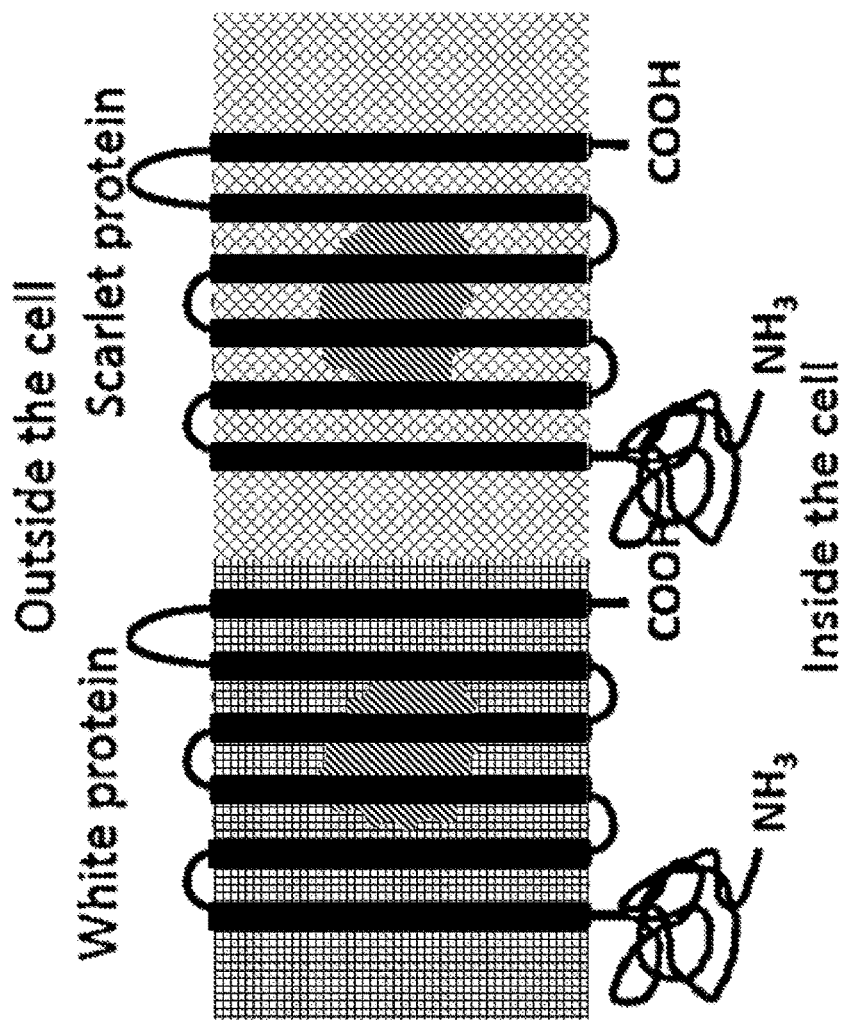

Fig. 8. Diagram of the Drosophila eye pigment transporters white and scarlet. Mutation of the white (w) or scarlet (st) genes disrupt pigment transport into the eye. Mutations in st prevents brown pigment transport and results in scarlet eyes. Most mutations in w prevents red and brown pigment transport and results in white eyes; some w mutants disrupt only brown pigment transport resulting in red eyes. Similar phenotypes are found in B. tabaci after CRISPR Cas9 mutagenesis of w or st.

FIG. 12

| Stage | Numbers/% |
|---|---|
| No. of Injections | 2640 |
| No. of nymphs (% hatch) | 1120 (42.4) |
| No. adults (% inj., % nymph) | 204 (6.8, 18.2) |
| No. st adults (% inj., % nymphs, % adults) | 20 (0.8, 1.8, 9.8) |

Note the decline in survivorship to adulthood — in Drosophila two st alleles are lethal during larval development.

WT and *scarlet* mutant males
(equivalent age)

*scarlet* mutant male

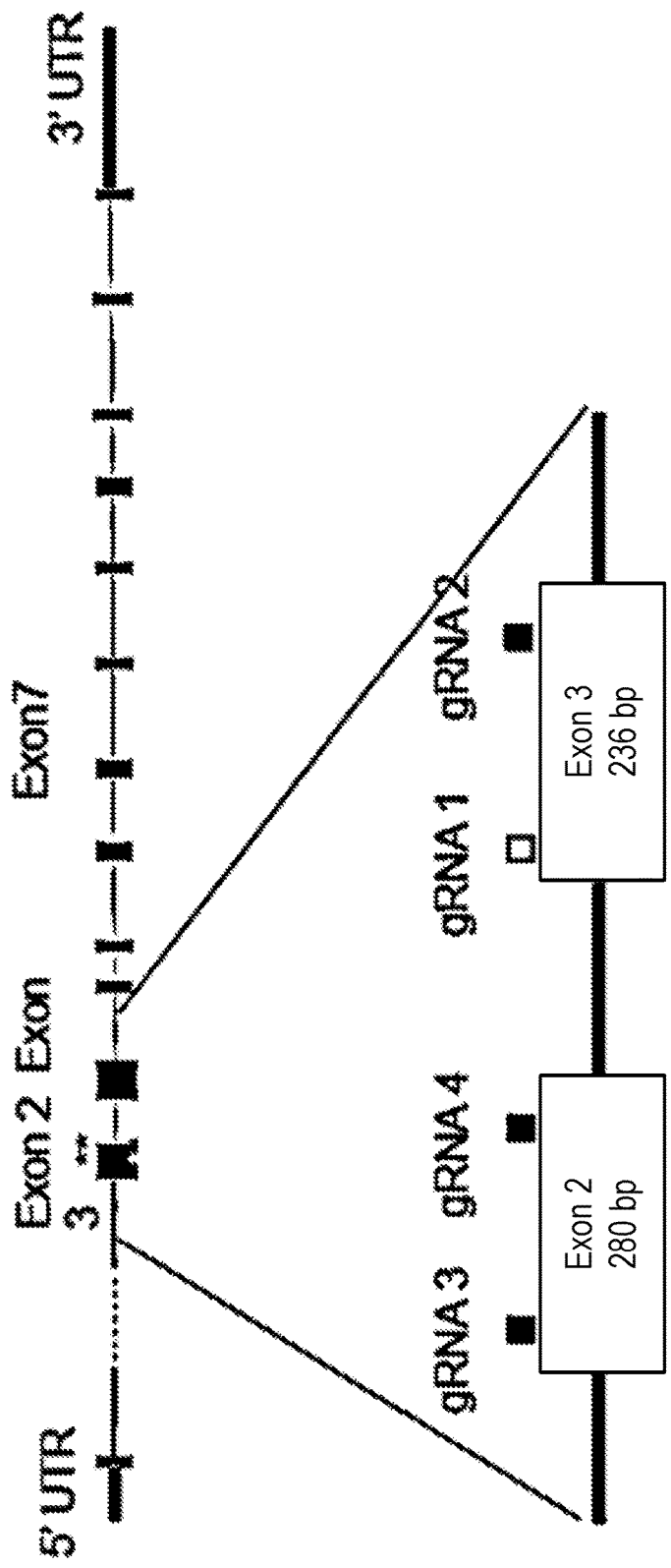
**Fig. 15A. Structure of the *B. tabaci* white gene (Bta05628).** Guide RNAs (gRNA1-4) targeting sequences with exon 2 and 3 were synthesized and introduced into *B. tabaci*. The cytoplasmic domain of the *white* transporter with its ATP binding site is encoded by exons 1-7, whereas the transmembrane domains are encoded by exons 7 to 13. (Fig 12). This figure is not to scale.

Fig. 15B. CRISPR-Cas9 *white* mutants. Guide RNAs (gRNA1-4) targeting sequences with exon 2 and 3 of Bta05628 were synthesized and introduced into *B. tabaci* with Cas9 by microinjection. The *w11-3* mutant male is shown with a sibling wild-type male. The total absence of eye color indicates integration early during embryogenesis. In some *w* injections, red-eyed males have been recovered.

FIG. 16A

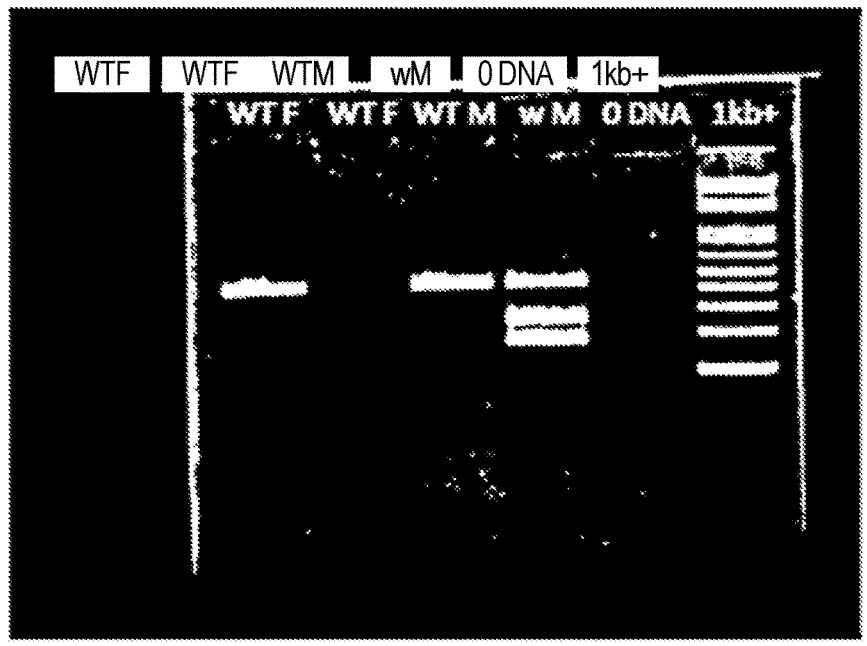

FIG. 16B

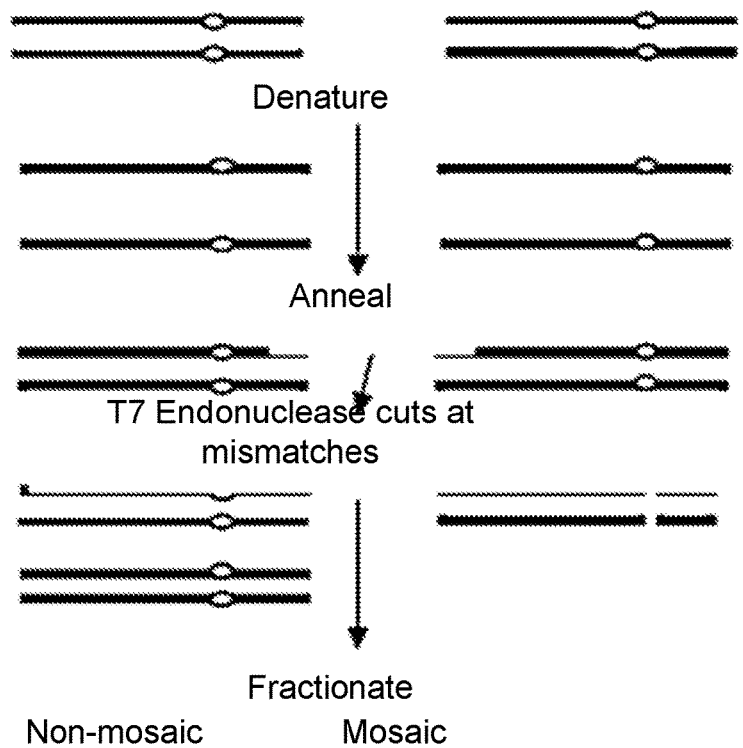

Figs. 16A and 16B. T7 Endonuclease Assay to identify DNA polymorphisms in a *white* male vs. 3 wild-type sibs. A schematic of the T7 endonuclease assay is shown to the right. A single band is detected in wild-type (WT) males and females, while multiple smaller bands, signifying changes in nucleotide composition, is detected in the white male. This male is a mosaic. A blank lane is indicated by 0 DNA and the 1-kb molecular mass ladder is displayed.

FIG. 17A

| ALLELE | SEQUENCE | # clones |
|---|---|---|
| Wild Type | 5' - CCAATAAACTCTACAACCTTGTCTCTCTCTGCCTATGTACAGCAAGAT - 3' | |
| Allele 1 | 5' - CCAATAAACTCTACAACCTTGT-TTCTCTCTGCCTATGTACAGCAAGAT - 3' | 1 |
| Allele 2 | 5' - CCAATAAACTCTACAACCTTGTCTCCAGTCTCTCTCTGCCTATGTACAGCAAGAT - 3' | 2 |
| Allele 3 | 5' - CCAATAAACTCTACAACCTTGTCTCTCTCTGCCTATGTACAGCAAGAT - 3' | 6 |
| Allele 4 | 5' - CCAATAAACTCTACAAC-----CTTCTCTCTGCCTATGTACAGCAAGAT - 3' | 13 |

Sequences the gRNA 2 region of the *white* gene recovered from the white-eyed mutant *w11-3*. The wild type sequence is shown for comparison. Of the 25 clones sequenced, 22 sequences from the *w11-3* male had mutations spanning single nucleotide to larger deletions, as well as nucleic acid substitutions. The CCT PAM site is indicated in red. The large number of mutant sequences implies mutagenesis occurred at a very early stage of embryonic development.

FIG. 17B

| | | |
|---|---|---|
| Wild Type | 5' | CCAATAAACTCTACAACCTTGTCTCTCTCTGCCTATGTACAGCAGAT 3' |
| Red allele | 5' | CCAATAAACTCTACAAC-----CTTCTCTCTGCCTATGTACAGCAGAT 3' |

Fig. 17B. Sequences across the gRNA 2 region of the *white* gene recovered from a red-eyed mutant w mutant. The wild type sequence is shown for comparison. The CCT PAM site in WT *B. tabaci* is indicated in red. Red-eyed males and females have been recovered with gRNA2.

FIG. 18A. Roots emerging from Brassica leaf discs. Roots have extensive root hairs. Often multiple independent roots develop from the same site.

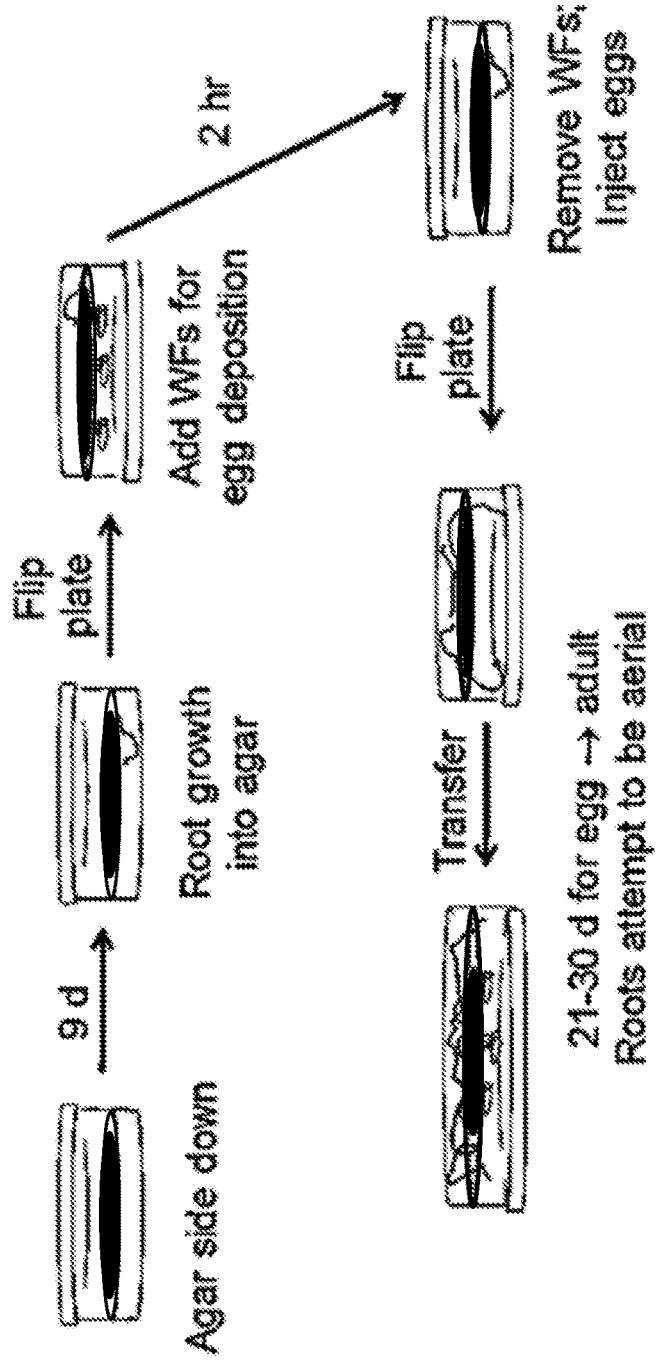
FIG. 19. Proposed pretreatment scheme for promoting adventitious roots. In addition to the initial incubation of plates with agar side down, phytohormones will be added to media for discrete periods of time to accelerate the timing of root formation as well as the number of roots formed.

FIG. 20A

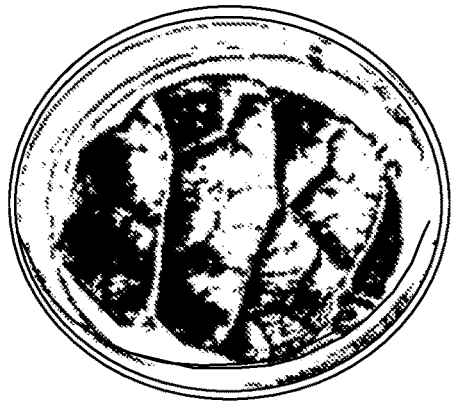
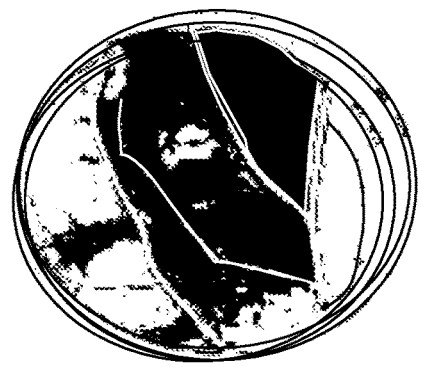

FIG. 20A. Color changes in discs without and with root systems. 61B-1 is a representative leaf disc with no roots. Yellowing and anthocyanin production is evident. 61B-3 is a representative leaf disc with roots. It is vividly green and has expanded to fill and exceed the dimensions of the 3.5-cm plate. Leaf buckling is evident due to its size.

FIG. 20B

FIG. 20B. Leaf disc plates viewed from the agar side to visualize root systems. The smaller size of the disc without roots (62B-2) vs the three discs with roots is shown. In addition the deep green color of discs with roots is also seen. Root systems are seen emanating from the edge of the discs into the center of the plate. Disc 61A-3 has a crack in the agar.

FIG. 21A

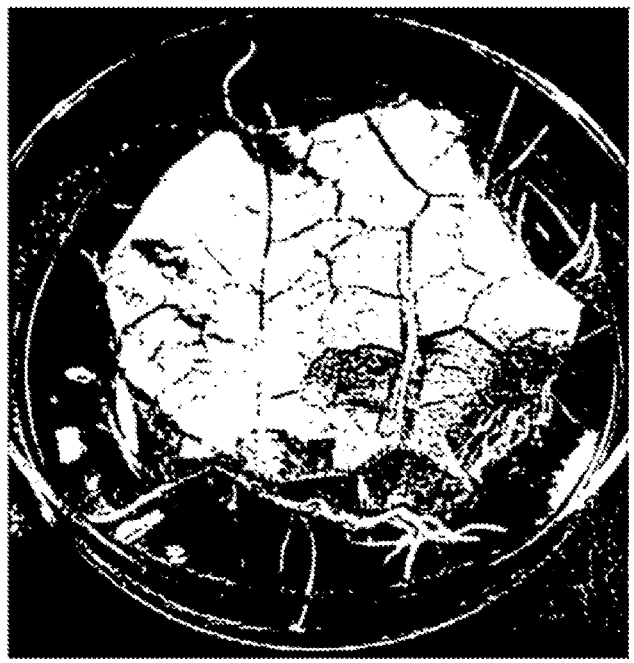

FIG. 21A. Growth in a 6.0-cm halo plate. A leaf disc with its root system in agar was transferred into a 6.0-cm halo plate. The plate was incubated agar side up for 2 days. Root growth into the ring of new agar in the halo plate and aerial orientation of roots is seen. There is one area of damage on this leaf (a water-soaked lesion).

FIG. 21B

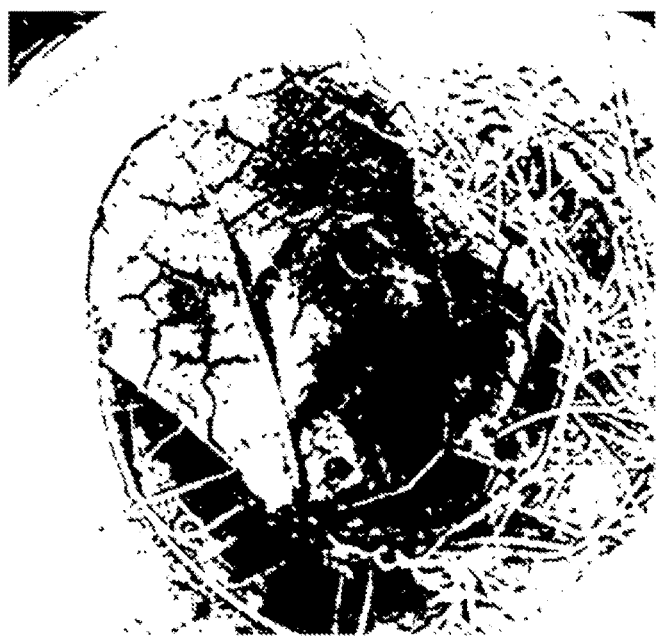

FIG. 21B. Growth in a 10-cm deep dish halo plate. The leaf disc in FIG. 17A with its root system was transferred from a 6.0-cm halo plate to a 10-cm deep halo plate. Note the extensive root system in the 6-cm region that is growing into the 10-cm ring of new agar. Note that the amount of anthocyanins (purple) has decreased. There is one area of damage (a water soaked lesion) that has dried up.

FIG. 22

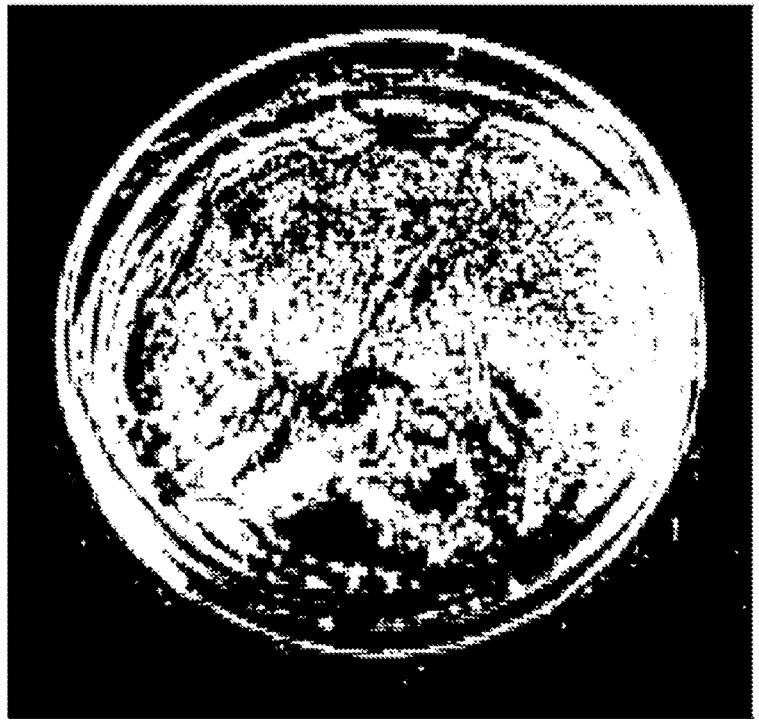

FIG. 22. Agar with eggplant leaf disc imprint.
The eggplant leaf discs make exceptionally strong contact with GB+GBV agar. The imprint that remains after disc removal is shown. Eggplant leaf blades have teeth that imbed in agar and cause cracking of the agar.

FIG. 23

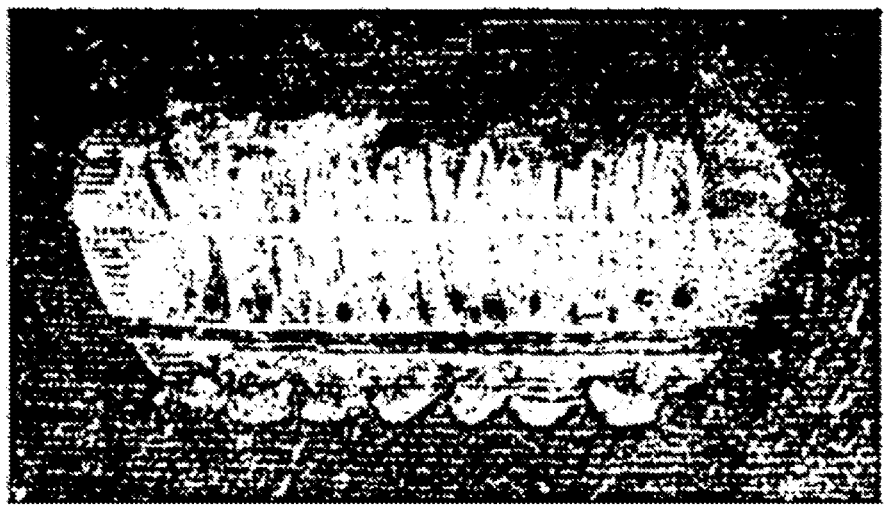

FIG. 23. Sorghum leaf segment with a GWSS egg raft. Sites of injection are seen as the dark melanized spots at the top of each egg. The red spots at the bottom of each developing egg are the eyes of the developing GWSS nymph.

METHOD FOR GENETIC MANIPULATION OF SAP-FEEDING INSECTS

CROSS-REFERENCE TO RELATED PATENT APPLICATIONS

This application is a U.S. National Phase Application Under Section 371 of PCT/US2019/012939, filed Jan. 9, 2019, which claims benefits of priorities to U.S. Provisional Patent Application No. 62/615,826, filed Jan. 10, 2018, and U.S. Provisional Patent Application No. 62/734,953, filed Sep. 21, 2018, which are incorporated by reference for all purposes.

FIELD OF THE INVENTION

The invention is related to the fields of insect genetics, pesticide development, entomology, insect rearing, genetic control strategies for IPM, virus vector transmission, host acceptance, and plant recognition of pest insects.

BACKGROUND OF THE INVENTION

The whitefly *Bemisia tabaci* is a species in the order Hemiptera. Most species in the order Hemiptera feed on plant sap located in the phloem of plants. The order Hemiptera includes many significant pests of global agriculture that are capable of damaging agriculture either by feeding or by transmission of pathogenic viruses to plants. These pests are responsible for more than 50% of the plant pathogens transmitted by insects (FIG. 1). Hemipteran species undergo incomplete metamorphosis. In the case of whiteflies and many other sap-feeding insects, metamorphosis occurs on plant leaves. Genetic technologies offer new approaches to pest insect control through the identification of gene and protein targets for chemical insecticides, developing genetic control strategies based on gene editing, gene drive, or genetic transformation, and generating enhanced immune responses to hemiptera and the plant pathogenic viruses the plants transmit.

Genetic technologies also provide tools by which the feeding preferences of whiteflies and other sap-feeding insects can be determined. At present, heritable genetic technologies have not been developed for any Hemipteran species despite the considerable impact these technologies have had on *Drosophila* genetics, as well as on mosquito and silkworm genetics. The absence of heritable genetic technologies in sap-feeding insects including the hemiptera, and most specifically in whiteflies, psyllids, glassy winged sharpshooter, and aphids, is the major roadblock preventing the deployment of modern genetic solutions to global problems in agriculture caused by these pest species (FIG. 2).

The current solutions to the control of whiteflies and other hemipteran species rely on the application of chemical insecticides. As most chemical insecticides are not specific to the targeted insects, targeted insects often develop resistance of these pesticides. Thus, chemical insecticides are often only effective for a relatively short period of time and can leave toxic residues in the environment. Furthermore, whitefly eggs and nymphs occur predominately on the underside of leaves, making topical insecticides ineffective. The major hurdle to the development of genetic technologies in whiteflies has been the introduction of macromolecules to whiteflies. Further, a cost-effective method that enables the rearing of genetically engineered strains of whiteflies in a confined, secure environment is also needed. The present invention addresses these and other needs.

BRIEF SUMMARY OF THE INVENTION

In one aspect, the invention features methods of rearing insects (e.g., sap-feeding insects) in the family Aleyrodidae (in particular, whiteflies in the genus *Bemisia*) by placing insects (e.g., sap-feeding insects) on a leaf-disc plate. In some embodiments, the sap-feeding insects are Glassy-winged sharpshooters. In some embodiments, the leaf-disc plate comprises between 1 to 80 insects (e.g., sap-feeding insects) per $cm^2$ of the leaf-disc plate (see, e.g., FIG. 4). In some embodiments, the method comprises placing the sap-feeding insects on a leaf-disc plate, wherein the sap-feeding insects are in the family Aleyrodidae, and the leaf-disc plate comprises a leaf-disc on a solid substrate. In some embodiments, the method may comprise: placing the sap-feeding insects on a leaf-disc plate, wherein the sap-feeding insects are in the family Aleyrodidae, and wherein the leaf-disc plate comprises a leaf-disc on a solid substrate; and a surface sterilizing step. In some embodiments, the surface sterilizing step may comprises washing the leaf-disc with a solution comprising 70% ethanol and 0.24% sodium hypochlorite. In some embodiments, the solid substrate is plant agar. In some further embodiments, the plant agar is supplemented with Gamborg's media and a vitamin supplement comprising GB+GBV. In some embodiments, the plant agar is supplemented with Gamborg's media, a vitamin supplement comprising GB+GBV, and has a pH of at least 5.0 but no greater than pH 7.0. In some embodiments, the plant agar is supplemented with Gamborg's media, a vitamin supplement comprising GB+GBV, and a phytohormone. In some embodiments, the plant agar is supplemented with Gamborg's media, a vitamin supplement comprising GB+GBV, a one or more phytohormones, and has a pH of at least 5.0 but no greater than pH 7.0. In some embodiments, the plant agar is supplemented with Gamborg's media, a vitamin supplement comprising GB+GBV, an indoleacetic acid phytohormone, and has a pH of at least 5.0 but no greater than pH 7.0. In some embodiments, the plant agar is supplemented with Gamborg's media, a vitamin supplement comprising GB+GBV, a indolebutryic acid phytohormone, and has a pH of at least 5.0 but no greater than pH 7.0. In some embodiments, the plant agar is supplemented with Gamborg's media, a vitamin supplement comprising GB+GBV, a 1-napthaleneacetic acid phytohormone, and has a pH of at least 5.0 but no greater than pH 7.0. In some embodiments, the method results in a leaf with increased health compared to a standard insect rearing method. In some embodiments, the method results in a leaf that has an increased lifespan compared to a standard insect rearing method. In some embodiments, the leaf-disc plate comprises a *Brassica* leaf, a citrus leaf, eggplant leaf, or a tomato leaf, and a solid substrate (e.g., plant agar). The leaf-disc plate may further comprise an antifungal agent. Both tomato and citrus can be successfully maintained on leaf-disc plates. Other plant candidates include, but are not limited to: eggplant, cotton, bean, cowpea, lettuce, squash, potato, cucumber, peppers, poinsettia, hibiscus, soybean, wheat, barley, maize, rice, cannabis, grapes, and cassava. As the host range of insects (e.g., sap-feeding insects) is broad, numerous additional plants with agricultural, horticultural, and ecological significance could be useful in the leaf-disc plate assay. In some embodiments, the sap-feeding insect are whiteflies (e.g., *Bemisia tabaci*). In addition, other hemipteran species such as psyllids, aphids, sharpshooters, leaf hoppers, and Bagrada bugs which lay their eggs attached to the leaf or stem surface, for example, may also be used.

In another aspect, the invention features methods of manipulating the genome of a sap-feeding insect (e.g., whitefly (e.g., *Bemisia tabaci*)) by injecting one or more nucleic acids and/or proteins into the sap-feeding insect by microinjection, wherein the sap-feeding insect is in the family Aleyrodidae. The methods include, for example, manipulating the genome of the sap-feeding insect using a genome-editing system, such as the CRISPR/Cas9 system, wherein the genome-editing system alters (e.g., inhibits) the expression of a target gene in the sap-feeding insect genome. Some genes that may be used to manipulate the genome of a sap-feeding insect (e.g., whitefly (e.g., *Bemisia tabaci*)) include, but are not limited to: vestigial (vg), white (w) and scarlet (st) genes, which impact wing development and eye color, respectively. For example, genes impacting whitefly biology include, e.g., genes expressed in the whitefly salivary glands that interfere with the host plant's defense system (e.g., whitefly effectors), genes expressed in whitefly tissues that are essential for the transmission of pathogenic plant viruses through the whitefly, whitefly genes that are involved in host plant choice, and whitefly genes that are involved in developmental disorders in plants, and genes that are essential for growth and development through all life stages. In some embodiments, nucleic acids that may be introduced into the sap-feeding insect by microinjection include, but are not limited to: DNA, an siRNA, an miRNA, and a gRNA. In some embodiments, the sap-feeding insect are whiteflies (e.g., *Bemisia tabaci*). In addition, other hemipteran species such as psyllids, aphids, sharpshooters, leaf hoppers, and Bagrada bugs which lay their eggs attached to the leaf or stem surface, for example, may also be used.

In another aspect, the invention features an assay system for testing the effect of a chemical on an insect comprising: a leaf-disc; an agar; and a solution comprising Gamborg's media and GB+GBV. In some embodiments, the assay system may comprise a leaf-disc; an agar; and a solution comprising Gamborg's media and GB+GBV; and a phytohormone. In some embodiments, the assay system may comprise a leaf-disc; an agar; and a solution comprising Gamborg's media and GB+GBV; and an auxin phytohormone selected from an indoleacetic acid, an indolebutyric acid, a 1-napthaleneacetic acid, or a combination thereof. In some embodiments, the assay system may comprise a leaf-disc; an agar; and a solution comprising Gamborg's media and GB+GBV; and a solution for surface sterilization. In some embodiments, the assay system may comprise a leaf-disc; an agar; and a solution comprising Gamborg's media and GB+GBV; a phytohormone; and a solution for surface sterilization. In some embodiments, the assay system may comprise a leaf-disc; an agar; and a solution comprising Gamborg's media and GB+GBV; a phytohormone; and a sterilization solution comprising 70% ethanol and 0.24% sodium hypochlorite. In some embodiments, the agar is a plant agar. In some embodiments, the assay system may be used for testing the effect of a pesticide on an insect. In some embodiments, the assay system may be used for testing the effect of an insecticide on an insect. In some embodiments, the assay system may be used for testing the effect of a pheromone on an insect. In some embodiments, the leaf-disc comprises a *Brassica*, a citrus leaf, a tomato leaf, or an eggplant leaf. In some embodiments, the insects are whiteflies (e.g., *Bemisia tabaci*). In addition, other hemipteran species such as psyllids, aphids, sharpshooters, leaf hoppers, and Bagrada bugs which lay their eggs attached to the leaf or stem surface, for example, may also be used. In some embodiments, the insects are Glassy-winged sharpshooters.

BRIEF DESCRIPTION OF THE DRAWINGS

FIG. 8 is a schematic showing the structure of the ABC transporter proteins encoded by the scarlet and white genes.

FIG. 12 shows a table summarizing scarlet injections into *B. tabaci*.

FIG. 15A is a schematic showing the locations of the four white gRNAs in the white gene of *Bemisia tabaci*.

FIGS. 16A and 16B show a T7 endonuclease assay demonstrating the mutation located in the gRNA2 target site of the w gene of the white-eyed mutant male from FIG. 14 (lane 4). Non-mutated gRNA2 target site DNA from the w gene of the wild-type male from FIG. 14 is shown in lane 3. Two wild-type females are shown in lanes 1 and 2. A molecular weight ladder is in lane 5.

FIG. 17A shows the sequences of wild type DNA and four mutant alleles generated at the gRNA2 site of the w gene in DNA prepared from the white-eyed male from FIG. 14. The location of the mutations in the four alleles downstream from the PAM site within the gRNA2 target site is consistent with genome editing mediated by the CRISPR/Cas9 system. FIG. 17B shows the sequence of a red-eyed mutant at the gRNA2 site of the w gene in DNA prepared from a male with bright red eyes. The location of this mutation downstream from the PAM site within the gRNA2 target site is consistent with genome editing mediated by the CRISPR/Cas9 system.

FIG. 19 is a schematic showing a pretreatment method provided by the present disclosure.

FIG. 20A is a photograph showing the color of a *Brassica* leaf disc grown on a phytoagar GB+GBV media with no root growth or with root growth. Leaf disc expansion is also seen in this figure.

FIG. 20B is a photograph showing leaf-disc plate (agar side down) to display a root systems formed from a *Brassica* leaf discs grown with a phytoagar GB+GBV media.

FIG. 21A a photograph showing a rooting leaf-disc system that was transferred to a 6.0-cm halo plate.

FIG. 21B a photograph showing a rooting leaf-disc system that was transferred from a 6.0-cm halo plate (shown in FIG. 21A) to a larger 10.0-cm halo plate.

FIG. 22 shows a picture of an eggplant leaf-disc grown on the leaf-disc system with GB+GBV media. The leaf disc was removed to show the intimate imprint of the eggplant disc remaining on the media.

FIG. 23 shows a picture of an injected and reared Glassy-winged sharpshooter using the methods provided by the present disclosure.

DETAILED DESCRIPTION OF THE INVENTION

The methods described herein are directed to rearing whiteflies (e.g., *Bemisia tabaci*) on a leaf-disc plate and genetic manipulations of the whitefly genome by, e.g., CRISPR/Cas9 system. The methods can be used, for example, to render the whiteflies more susceptible to chemical insecticides, to change the feeding preference of whiteflies, and/or to alter the host range, insect performance, and plant perception of insect infestation.

I. Methods of Rearing Whiteflies

Figure 1:
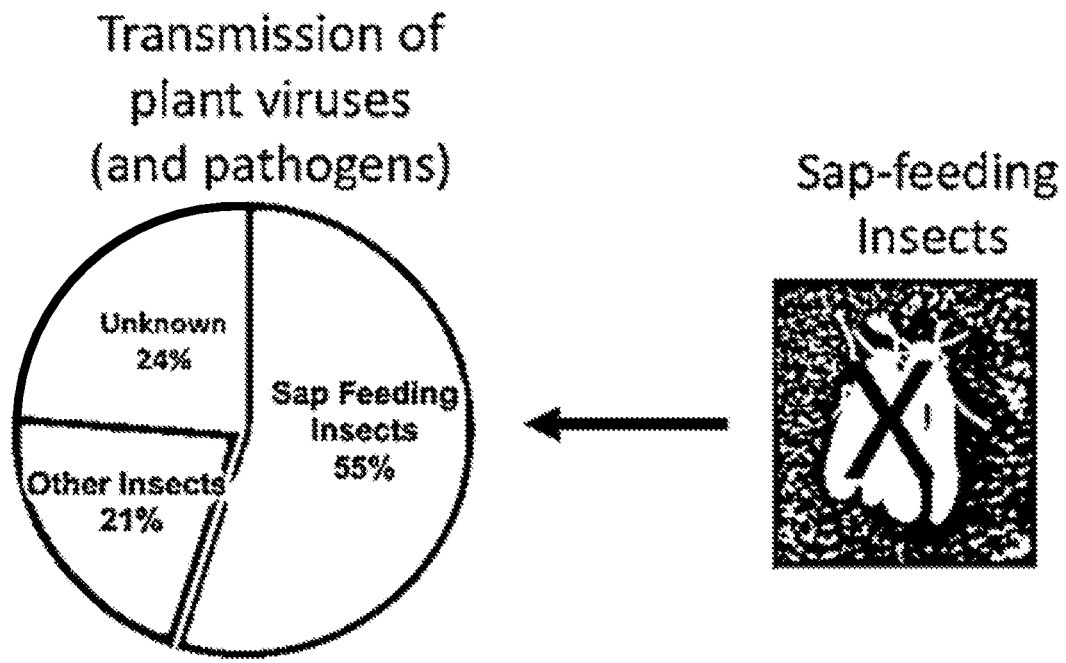
FIG. 1 is a schematic showing the transmission of plant viruses by various insects.
Figure 2:
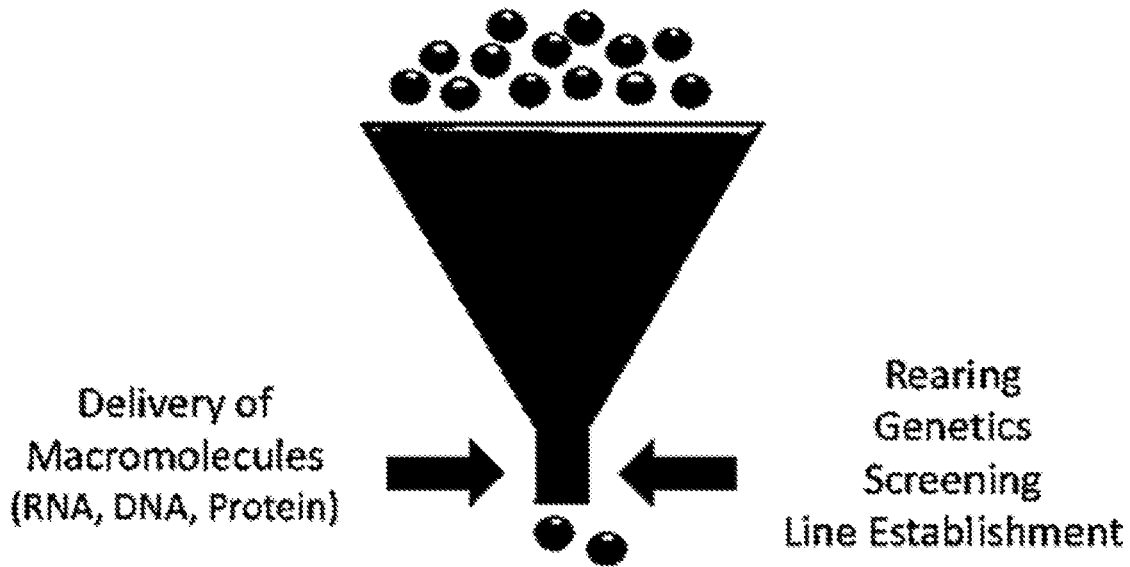
FIG. 2 is a schematic showing current technical challenges that limit the use of genetic technologies.
Figure 3:
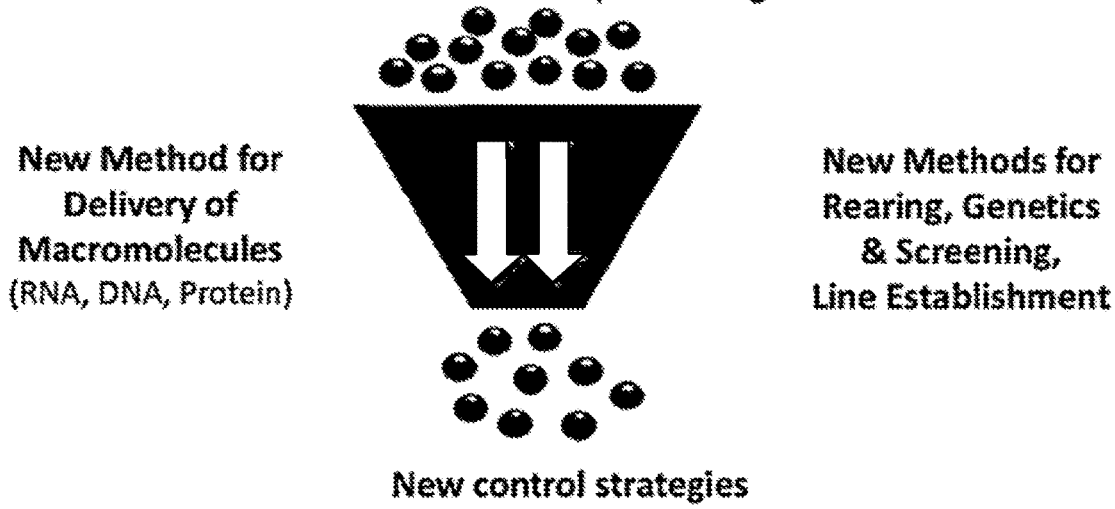
FIG. 3 is a schematic showing new methods and strategies to control sap-feeding insects.
Figure 4:
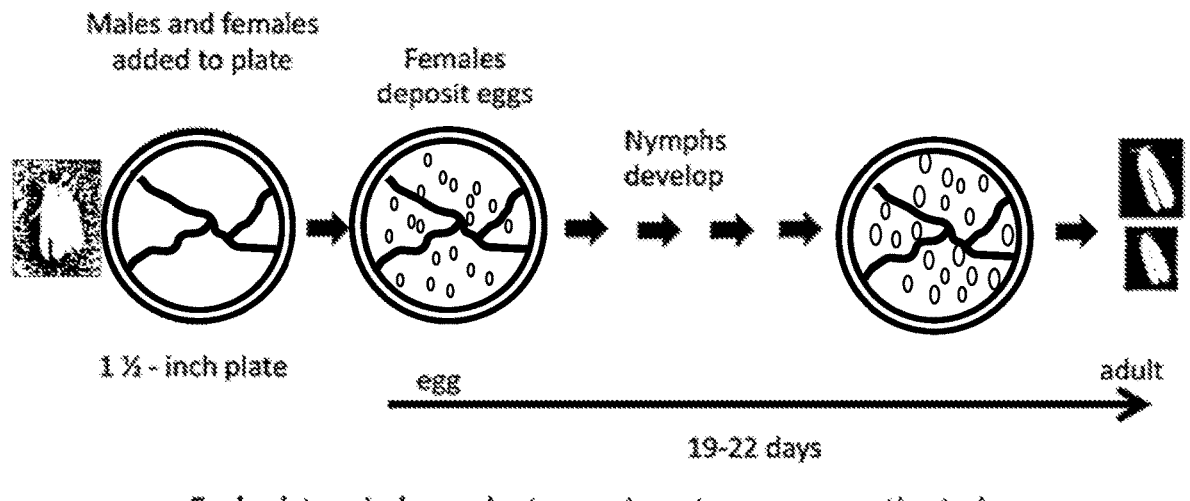
FIG. 4 is a schematic describing a whitefly-rearing system that has a small footprint, cost-effective, and scalable.

The invention provides methods of rearing whiteflies from egg to adult using a leaf-disc plate (FIG. 3 and FIG. 4). Although the following discussion focuses on whiteflies in the genus *Bemsia*, one of skill will recognize that the methods of rearing and genetic manipulation can be applied to other members of the Aleyrodidae family that include, but are not limited to: members of the following genera: *Acanthobemisia* (e.g., *Acanthobemisia distylii* and *Acanthobemisia indicus*), *Aleurotrachelus socialis*, *Apobemisia* (e.g., *Apobemisia celti* and *Apobemisia kuwanai*), *Asterobcmisia* (e.g., *Asterobemisia atraphaxius*, *Asterobemisia carpini*, *Asterobemisia curvata*, *Asterobemisia dentate*, *Asterobemisia lata*, *Asterobemisia obenbergeri*, *Asterobemisia paveli*, *Asterobemisia salicaria*, *Asterobemisia silvatica*, *Asterobemisia* takahashii, *Asterobemisia trifolii*, and *Asterobemisia yanagicola*), *Bemisaleyrodes* (e.g., *Bemisaleyrodes balachowskyi*, *Bemisaleyrodes brideliae*, *Bemisaleyrodes grjebinei*, and *Bemisaleyrodes pauliani*), *Bemisia* (e.g., *Bemisia tabaci* species complex (comprising 35 species), *Bemisia afer*, *Bemisia alni*, *Bemisia antennata*, *Bemisia bambusae*, *Bemisia berbericola*, *Bemisia capitate*, *Bemisia caudasculptura*, *Bemisia centroamericana*, *Bemisia combreticula*, *Bemisia confuse*, and *Bemisia cordylinidis*), *Bemisiella* (e.g., *Bemisiella artemisiae* and *Bemisiella lespedezae*), *Heterobemisia* (e.g., *Heterobemisia alba*), *Metabemisia* (e.g., *Metabemisia distylii*, *Metabemisia filicis*, and *Metabemisia palawana*), and *Parabemisia* (e.g., *Parabemisia aceris*, *Parahemisia indica*, *Parabemisia jawani*, *Parabemisia lushanensis*, *Parabemisia maculate*, *Parabemisia myricae*, *Parabemisia myrmecophila*), and *Trialeurodes* (e.g., *Trialeurodes vaporarium*, *Trialeurodes viribalis*, etc.). Other sap-feeding insects including members of other genera within hemiptera, for example, aphids psyllids, sharpshooters, and leafhoppers. These species include the Glassy Winged Sharp Shooter (GWSS, *Homalodisca coagulata*), Asian Citrus Psyllid (ACP, *Diaporhorina citri* Kuwayama), the potato/tomato psyllid (*Bactericerca cockerelli* (Sulc)), Bagrada bug, the beet leafhopper (*Circulifer tenellus*), and any insect species in which the egg is accessible and attached to the leaf surface.

In some embodiments, having the appropriate density of whiteflies on a leaf-disc plate used in methods described herein may be conducive to the growth and health of the whiteflies and the plant leaf-disc. In some embodiments of the methods, there may be between 1 and 80 whiteflies per $cm^2$ of the leaf-disc plate. The leaf-disc plate may be constructed using a *Brassica* leaf, a sorghum leaf, a citrus leaf, a tomato leaf, an eggplant leaf, or a plant agar (e.g., 0.5%-2% plate agar; e.g., 1% plate agar) (see, e.g., Example 1).

In some embodiments, nutritional supplements such as Murishige and Skoog media may be added to the plant agar of leaf-disc plate. In other embodiments, Gamborg's media may be added to the leaf-disc plate. Gamborg's media has been described in Gamborg O L, et al. (1968) Nutrient requirements of suspension cultures of soybean root cells. Experimental Cell Research 50 (1): 151-158, and in herein incorporated by reference in its entirety for all purposes. In a further embodiment, the media may be further supplemented by vitamins (e.g., GB+GBV or the like). In some embodiments, Gamborg's media and a vitamin supplement comprising GB+GBV is added to the leaf-disc plate.

In some embodiments, the plant agar of the leaf-disc may comprise a phytohormone. In some cases the phytohormone is an auxin. In some embodiments, the phytohormone is an indoleacetic acid. In some embodiments, the phytohormone is an indolebutryic acid. In some embodiments, the phytohormone is a 1-napthaleneacetic acid. In some embodiments, the phytohormone is a combination of more than one auxin, as provided herein. In some embodiments, the plant hormones, and/or plant growth regulators (e.g., cytokinins, abscisic acid, gibberellic acid, jasmonic acid, and salicylic acid, etc.) may also be used.

In some applications, it may be useful to adjust the pH of the leaf-disc plate system depending on the type of plant used and/or insect to be reared. In some embodiments, the pH of the leaf-disc system is at least about 5.0-5.2, 5.3-5.5, 5.6-5.8, 6.0-6.2, or 6.3-6.5 but no greater than about pH 7.0. In some embodiments, the pH of the leaf-disc system is at least about pH 5.8 but no greater than about pH 7.0.

In some embodiments, the method can further comprise adding a surface sterilization solution to wash the disc leaf. In some cases, the surface sterilization is applied as a pretreatment. In some cases the surface sterilization is applied during the growing phase of the leaf-disc. In some embodiments, the surface sterilization may comprise an ethanol-based solution. In some embodiments, the surface sterilization may comprise sodium hypochlorite. In some embodiments, the surface sterilization may comprise ethanol and sodium hypochlorite. In some embodiments, the surface sterilization may comprise 70% ethanol and 0.24% sodium hypochlorite.

In some embodiments, to prevent potential fungal growth, an antifungal agent that does not interfere with the growth and health of the whiteflies or leaf may be applied to the leaf-disc plate. Examples of antifungal agents include, but are not limited to: amphotericin B, micanazole, benzimidazole, nipagin anidulafungin, caspofungin, micafungin, candicidin, filipin, natamycin, nystatin miconazole, bifonazole, clotrimazole, econazole, ketoconazole, and oxiconazole.

The antifungal agent may be dissolved in an appropriate solvent (e.g., dimethyl sulfoxide (DMSO) or water) that is not toxic to either the insects or the leaf-disc.

The leaf-disc plate containing the whiteflies may be placed in an incubator with the appropriate temperature and humidity settings. In some embodiments, the temperature may be between 25° C. and 35° C. (e.g., 28° C.). The percentage of humidity of the incubator may be at least 70% (e.g., between 75% and 90%). Further, the incubator may be equipped with fluorescent lamps to establish a day/night cycle that is conducive to whitefly and leaf-disc growth and for the screening of whiteflies.

II. Methods of Manipulating the Whitefly Genome

The methods described herein include methods for manipulating the genome of whiteflies. Methods of introducing nucleic acids into the genome of insects using, for example, microinjection techniques, are known. Such techniques can be used to introduce any nucleic acid and/or protein of interest including, for example, transposons, DNA encoding desired proteins, DNA encoding RNA molecules useful in RNAi techniques (e.g., siRNA, miRNA, and the like), nucleic acids encoding nucleases, and guide RNAs useful in genome-editing systems (e.g. the CRISPR/Cas9 system), as well as other Cas proteins and other proteins leading to DNA recombination. Examples include, but are not limited to: transposases, integrases, and site-specific recombinases. The introduced nucleic acids can confer a variety of traits to the whiteflies. For example, the techniques may render the whiteflies more susceptible to chemical insecticides, modify the immune response of whiteflies to plant pathogenic viruses, eliminate whitefly effectors and thereby increase host plant resistance to whiteflies, change the feeding preference of whiteflies, and/or alter the ability of whiteflies to grow and develop. These techniques can also be applied to other sap-feeding insects that lay eggs affixed to leaves, including, but are not limited to: psyllids, sharpshooters, leafhoppers, aphids, Bagruda bug, Lygus bug, box elder bugs, chili thrips, crape myrtle bark scale, four-lined plant bug, pink hibiscus mealybug, scale insects, cycad aulacaspis scale, and wax scales on holly. In some embodiments, RNAi or genome-editing techniques may be used to knock out or knock down the expression of a target gene in the whiteflies. Examples of target genes include, e.g., vestigial (vg) gene, and scarlet (st) gene and white (w) gene that impact wing development and eye color, respectively.

A number of methods can be used to suppress or silence gene expression in an insect. The ability to suppress gene function in a variety of organisms, using double-stranded (ds) RNA is well known. RNAi (e.g., siRNA, miRNA) appears to function by base-pairing to complementary RNA or DNA target sequences. When bound to RNA, the inhibitory RNA molecules trigger either RNA cleavage or translational inhibition of the target sequence.

A short hairpin RNA or small hairpin RNA (shRNA) is an artificial RNA molecule with a hairpin turn that can be used to silence target gene expression via the small interfering RNA (siRNA) it produced in cells. Expression of shRNA in cells is typically accomplished by delivery of plasmids or through viral or bacterial vectors. Once the vector has integrated into the host genome, the shRNA is then transcribed in the nucleus typically by RNA polymerase II or RNA polymerase III. The resulting pre-shRNA is exported from the nucleus and then processed by the Dicer enzyme and loaded into the RNA-induced silencing complex (RISC). The sense strand is degraded by RISC and the antisense strand directs RISC to an mRNA that has a complementary sequence. An AGO protein in the RISC then cleaves the mRNA, or in some cases, represses translation of the mRNA, thus, leading to its destruction and an eventual reduction in the protein encoded by the mRNA. Thus, the shRNA leads to targeted gene silencing. shRNA is an advantageous mediator of siRNA in that it has relatively low rate of degradation and turnover.

MicroRNAs (miRNAs) are noncoding RNAs of about 19 to about 24 nucleotides in length that are processed from longer precursor transcripts that form stable hairpin structures. miRNAs base pair with complementary sequences within the mRNA transcript. As a result, the mRNA transcript may be silenced by one or more of the mechanisms such as cleavage of the mRNA strand, destabilization of the mRNA through shortening of its poly(A) tail, and decrease translation efficiency of the mRNA transcript into proteins by ribosomes. In some embodiments, miRNAs resemble the siRNAs of the shRNA pathway, except that miRNAs derive from regions of RNA transcripts that fold back on themselves to form short hairpins, which are also called pri-miRNA. Once transcribed as pri-miRNA, the hairpins are cleaved out of the primary transcript in the nucleus by an enzyme called Drosha in association with the RNA binding protein GRC8. The hairpins, or pre-miRNA, are then exported from the nucleus into the cytosol. In the cytosol, the loop of the hairpin is cleaved off by the Dicer enzyme. The resulting product is now a double-stranded RNA with overhangs at the 3' end, which is then incorporated into RISC. Once in the RISC, the second strand is discarded and the miRNA that is now in the RISC is a mature miRNA, which binds to mRNAs that have complementary sequences.

Genome-editing systems are well known in the art. The particular genome-editing protein used is not critical, so long as it provides site-specific targeting of a desired nucleic acid sequence. Exemplary genome-editing proteins include targeted nucleases such as engineered zinc finger nucleases (ZFNs), transcription-activator like effector nucleases (TALENs), and engineered meganucleases. In addition, the systems which rely on an engineered guide RNA (a gRNA) to guide a nuclease (e.g., Cas9) to a target cleavage site can be used. The most commonly used system is the CRISPR/Cas9 system, which includes a Cas protein and at least one or two ribonucleic acids that are capable of directing the Cas protein to and hybridizing to a target motif in the sequence of the targeted gene. Variants of the Cas protein that cleave a wider range of editing sites, or other proteins that can be used with single or multiple CRISPR guide RNAs (such as the Cpf1 enzyme from *Acidaminococcus* and *Lachnospiraceae* or C2c2 from Leptotrichia shahii) are also available. The Cas protein then cleaves the target motif and results in a double-strand break or a single-strand break. Such systems can be used for targeted disruption of a gene or to introduce a desired nucleic acid sequence to the target site. Any genome-editing system that is capable of altering a target polynucleotide sequence in a cell can be used in methods described here. In some embodiments, the CRISPR/Cas9 system is a CRISPR type I system. In some embodiments, the CRISPR/Cas9 system is a CRISPR type II system. In some embodiments, the CRISPR/Cas9 system is a CRISPR type V system with the Cpf1 enzyme being an example of a type V system applicable to varieties of cell types and organisms.

The Cas protein used in the methods described herein can be a naturally occurring Cas protein or a functional derivative thereof. A "functional derivative" includes, but are not limited to: fragments of a native sequence and derivatives of a native sequence polypeptide and its fragments, provided that they have a biological activity in common with the corresponding native sequence polypeptide. Optimizing the codons of synthetic Cas or Cpf1 proteins to mimic the codon-usage of the target insect is also included. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas protein or a fragment thereof include but are not limited to mutants, fusions, or covalent modifications of Cas protein.

In some embodiments, the Cas protein used in methods described herein is Cas9, Cpf1, or a functional derivative thereof. In some embodiments, the Cas9 protein is from *Streptococcus pyogenes*. Cas9 contains two endonuclease domains, including a RuvC-like domain which cleaves target DNA that is noncomplementary to crRNA, and an HNH nuclease domain which cleaves target DNA complementary to crRNA. The double-stranded endonuclease activity of Cas9 also requires that a short conserved sequence (e.g., 2-5 nucleotides), known as a protospacer-associated motif (PAM), follows immediately after the 3' end of a target motif in the target sequence. The Cpf1 protein contains a RuvC-like domain, which generates a 4-5 bp single stranded overhang, and also requires a PAM site but one that differs in sequence from the PAM site recognized by Cas9.

The methods of the invention can also be used in genetic-based control strategies such as engineered gene-drive systems. Gene-drive systems have been used to force inheritance in a non-Mendelian fashion, allowing the gene-drive system to increase itself—and any linked genes—in frequency with each generation even without conferring fitness advantages to its host. Such systems include, for example, the Medea system in *Drosophila*.

II. Leaf-Disc Assay System

The present disclosure provides a leaf-disc assay system for assaying the affect of chemicals (e.g., pesticides, insecticides, pheromones, or the like) on an insect as provided herein. Generally, the user will supply the chemical to be applied to the leaf-disc assay system. In some embodiments, the leaf-disc assay system comprises a leaf-disc plate, a plant agar as provided herein, and a solution comprising a media such as, Gamborg's media, and vitamins such as, GB+GBV. In some embodiments, the leaf-disc assay system comprises a leaf-disc plate, a plant agar, and a solution comprising a media such as, Gamborg's media and vitamins such as GB+GBV, and a phytohormone such as an auxin. In a further embodiment, the assay system may comprise a surface sterilization solution as provided herein.

IV. Definitions

As used herein, the term "sap-feeding insects" refers to insects that use piercing and sucking mouth parts to feed on sap and stem of plants. Sap-feeding insects also lay their eggs attached to the leaf or stem surface of the plants. Examples of sap-feeding insects include, but are not limited to: whiteflies, psyllids, aphids, sharpshooters, leaf hoppers, and Bagrada bugs.

As used herein, the term "leaf-disc plate" refers to a surface containing a leaf on a solid substrate (e.g., a plant agar medium) used to rear sap-feeding insects. As demonstrated in Example 1, leaf-disc plates having various sizes (e.g., 1-10 cm) may be constructed. Phytoagar can be supplements with salts and carbon and nitrogen sources as needed. Murashige and Skoog media with and without sucrose may also be added. These can be supplemented with a variety of plant hormones (e.g., cytokinins, abscisic acid, gibberellic acid, jasmonic acid, and salicylic acid, etc.). Plates can also be supplemented with fungicides, e.g., amphotericin B, micanazole, benzimidazole, anidulafungin, caspofungin, micafungin, candicidin, filipin, natamycin, nystatin miconazole, bifonazole, clotrimazole, econazole, ketoconazole, and oxiconazole.

As used herein, the term "polynucleotide" refers to an oligonucleotide, or nucleotide, and fragments or portions thereof, and to DNA or RNA of genomic or synthetic origin, which may be single- or double-stranded, and represent the sense or anti-sense strand.

As used herein, the term "polypeptide" describes a single polymer in which the monomers are amino acid residues, which are joined together through peptide/amide bonds. A polypeptide is intended to encompass any amino acid sequence, either naturally occurring, recombinant, or synthetically produced.

EXAMPLES

Example 1: Rearing Whiteflies

Protocol a) A solution of 1% plant agar (Sigma) ("phytoagar") was sterilized and cooled. A volume of 4.5 mL of the agar was poured into sterile 3.5-cm petri dishes. Once set, the petri dishes were covered with lids, sealed with Parafilm®, and stored in a sealed plastic bag at 4° C.

b) A large, relatively mature leaf was removed from *Brassica*, eggplant, sorghum, citrus, or tomato and placed on a moistened paper towel. A sterile cutter was used to excise a leaf-disc with a diameter close to the internal diameter of the 3.5-cm plate. The leaf-disc was placed on the disc with its underside (abaxial surface) facing up. The leaf-disc was gently flattened across its surface to ensure that as much of it as possible was in contact with the phytoagar.

c) A mesh lid was placed on the 3.5-cm plate. This lid contained a hole about 2.5 cm in diameter over which a silk screen mesh of 60-100-μm pore size was placed and glued. The completed unit was termed a leaf-disc plate (LDP). Larger LDPs have also been prepared. For example, for 7-cm diameter petri dishes in which case the volume of phytoagar used was 9.5 mL.

d) About 50-100 adult whiteflies were placed on the LDP (3.5 cm).

e) The LDP was inverted and placed on a plastic rack inside a large tray so that there was air flow into each LDP.

f) The tray was placed in an incubator set at 28° C. with approximately 75%-80% humidity and a 14:10 day night cycle. Plant/aquaria fluorescent lamps were used.

g) The tray was covered with 2 layers of mesh.

h) The LDPs were monitored daily for: a) health of the insects and the stage of their lifecycle, b) the health of the leaf with respect to any fungal infections and drying, c) the amount and water content of the phytoagar, and d) the presence of fungus on the lid. Lids and phytoagar were changed as needed with clean, sterile lids and fresh phytoagar. The leaf-disc was gently removed from the original phytoagar and gently placed on the fresh phytoagar.

i) The LDPs were sprayed with fungicide on a weekly basis. Fungicide treatments were applied post-egg deposition.

j) Once eggs were seen on the phytoplates, the adults were immobilized by placing them at 4° C. for approximately 15 minutes. Adults were removed by aspiration.

k) Embryos were observed daily for signs of development through to hatching, typically at 5-7 days following oviposition.

l) Nymphs were observed daily for signs of development and health. They were also screened for relevant genetic markers.

m) Virgins (newly emerged adults) were collected every 12 hrs. These were placed at 28° C. and each virgin adult was sexed and screened for relevant genetic markers. These adults, in the desired numbers, sexes, or pairs, were then used to establish the next insect generation on LDPs of the appropriate size.

Figure 5A:
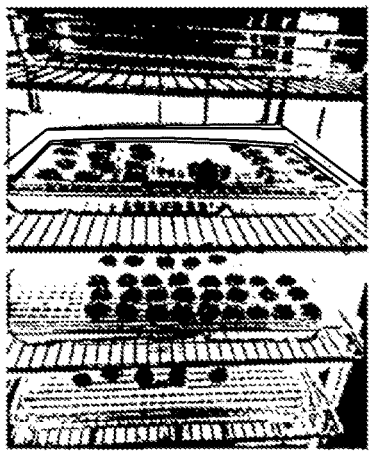
FIGS. 5A and 5B are photographs comparing whiteflies reared on leaf-disc plates and whiteflies reared in greenhouse facilities or large growth chambers with intact plants.
Figure 5B:
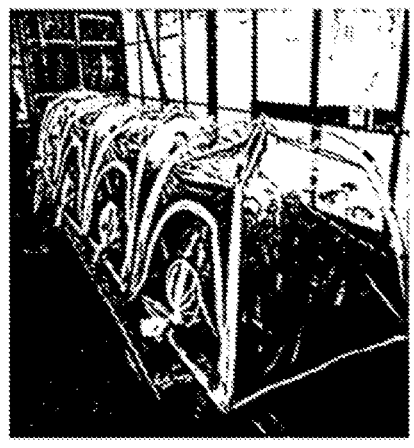

Subsequent generations of whiteflies were reared in this manner without the need for greenhouse facilities or large growth chambers with intact plants (FIGS. 5A and 5B). Multiple genetic strains could be reared within single incubators using this technology. The technology could be scaled up for the purpose of increasing the size of specific genetic strains for mass production. Using this technology, the egg-to-adult life cycle of whiteflies was completed in approximately 19-21 days and the egg-to-adult life cycle of the next generation was completed in approximately 30-40 days. We have leaf-discs that survived in excess of 30 days using this technology. LDP-raised insects can also be placed on plants with small footprints for a single generation.

Example 2: Introducing Nucleic Acids and Proteins into Whiteflies

Figure 6:
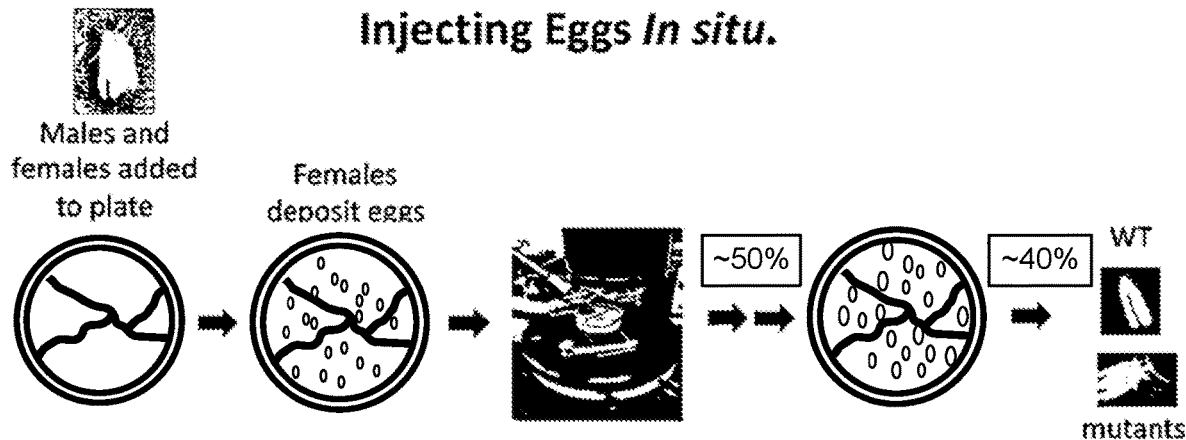
FIG. 6 is a schematic showing high efficiency of the injections.
Figure 7:
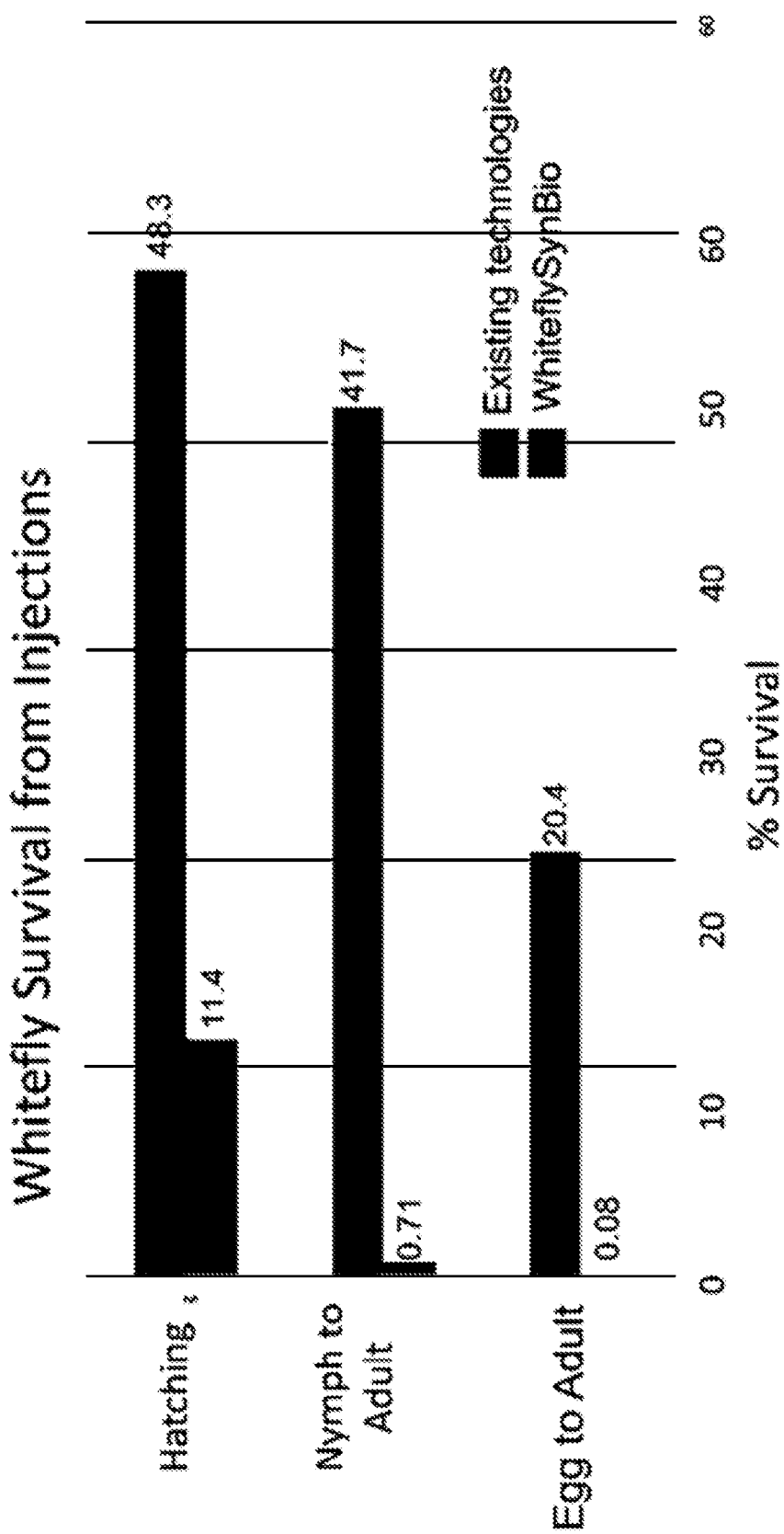
FIG. 7 is a graph comparing whitefly survival from current methods with other technologies.

Protocol (FIGS. 6 and 7)

a) A fresh LDP was prepared as described above in Example 1a-c.

b) Whiteflies were immobilized by placing at 4° C. for approximately 15 minutes, after which approximately 50 whiteflies were placed on the LDP.

c) The LDP was placed in an incubator at 28° C. for 1-5 hours (e.g., 2 hours).

d) The LDP was placed at 4° C. for approximately 15 minutes, after which all adults were removed by aspiration.

e) The freshly laid eggs from mated or non-mated females on the LDP were desiccated for a brief period of time (typically 3 minutes) by placing in a sealed chamber with Drierite®.

f) The LDP was placed on a circular rotating stage on an inverted or dissecting microscope.

g) A quartz needle was backfilled with DNA, RNA, and/or protein (Cas9) prepared in a buffer at the appropriate concentration. For genetic transformation experiments, the concentrations used were 300 ng/µL of helper plasmid and 150 ng/µL of vector plasmid. CRISPR/Cas9 injections were performed with a range of concentrations of guide RNAs and Cas9 protein with the protein range from 75-300 ng/µL and each guide RNA at 40 ng/µL. The parameters for the production of quartz needles using a Sutter Laser Needle Puller were: heat: 730, filament: 4, velocity: 40, delay: 125, and pull: 125. In other embodiments, silica and aluminoborosilicate needles can be used.

h) The quartz needle was placed into a micromanipulator.

i) The embryos on the LDP were microinjected in situ, as egg pedicels remained at their insertion site in the leaf-disc on the LDP. The stage was rotated to ensure that all embryos were microinjected. A picopump was used to provide pressurized air-driven delivery to the embryos. Injection pressures ranged from 10-40 psi and hold pressures ranged from 2-8 psi depending on the size of the aperture of the needle. In some embodiments, other microinjection methods (e.g., Femtojet or Piezo injector) can be used.

j) Once all embryos were microinjected, the LDP was removed from the stage. A lid with mesh was placed on the LDP, and the LDP was placed in the 28° C. incubator. The LDPs were monitored daily and managed as described above.

Example 3: Genomic-Editing Targeting Vestigial, Scarlet, and White Genes

Using this technology we have targeted three genes in *B. tabaci* for genome editing by the CRISPR-Cas9 system. One is the vestigial gene, mutations in which cause a range of phenotypes from embryonic lethality to malformed wings in adults. The second is the scarlet gene, which encodes a protein that transports the brown xanthommatin pigment from the cytoplasm into pigment granules of the cells. In *Drosophila melanogaster*, mutations in the scarlet gene result in flies with bright red eyes due to the absence of the xanthommatin. The third is the white gene which encodes a protein that transports both the xanthommatin and pterdine pigments from the cytoplasm into the pigment granules of the cells (FIG. 8). We injected Cas9 protein at a concentration of 300 ng/µl and scarlet, vestigial, or white guide RNAs (gRNAs) each at a concentration of 40 ng/µl into pre-blastoderm embryos approximately 2 hrs after oviposition onto *Brassica* leaves placed on phytoagar. Developing embryos, nymphs, and adults were scored during development.

Figure 9A:
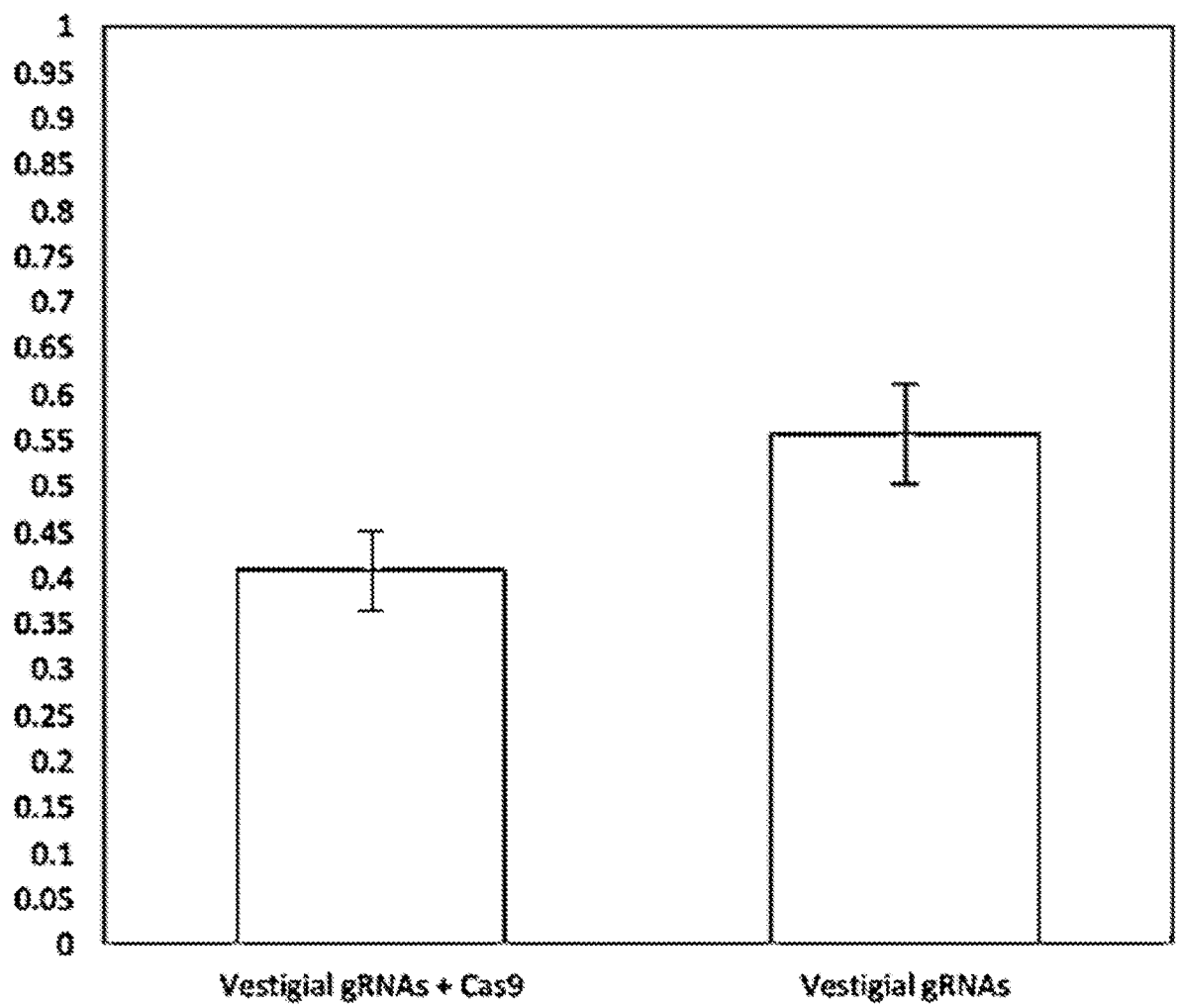
FIGS. 9A and 9B are graphs showing the success of creating vestigial mutants.
Figure 9B:
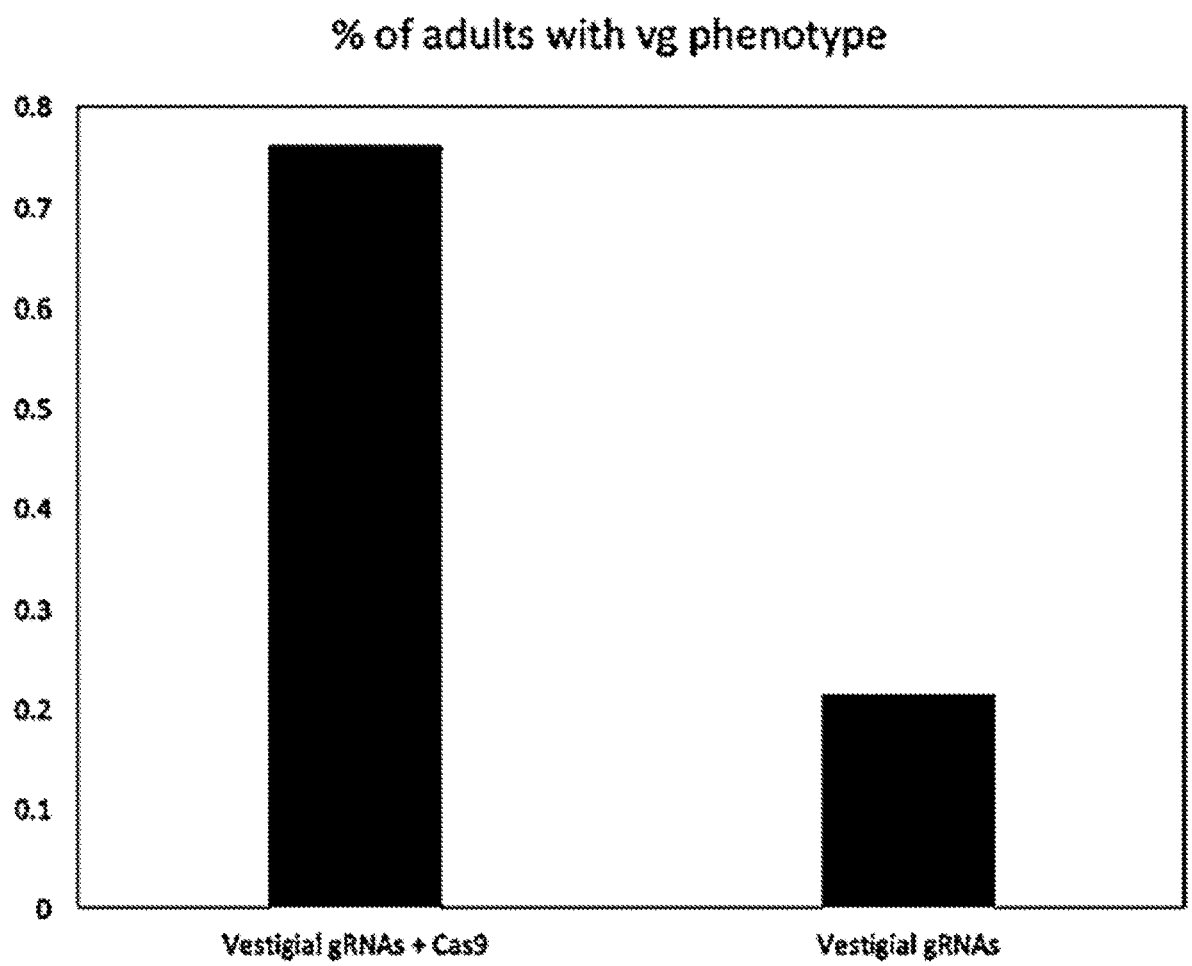
Figure 10:
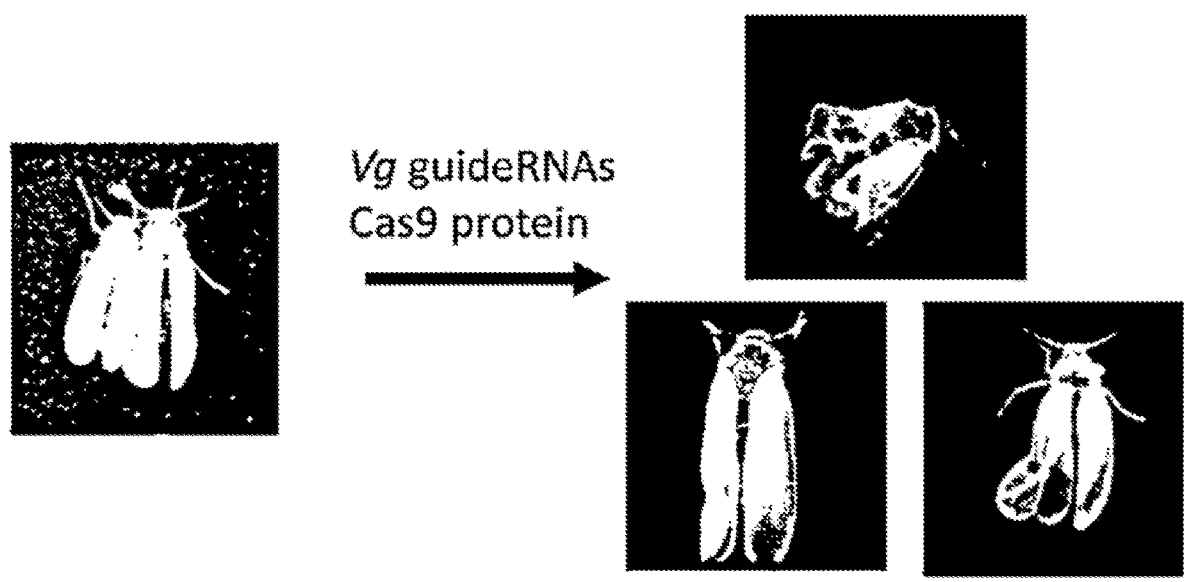
FIG. 10 shows photographs of vestigial mutant whiteflies with deformed wings.
Figure 11:
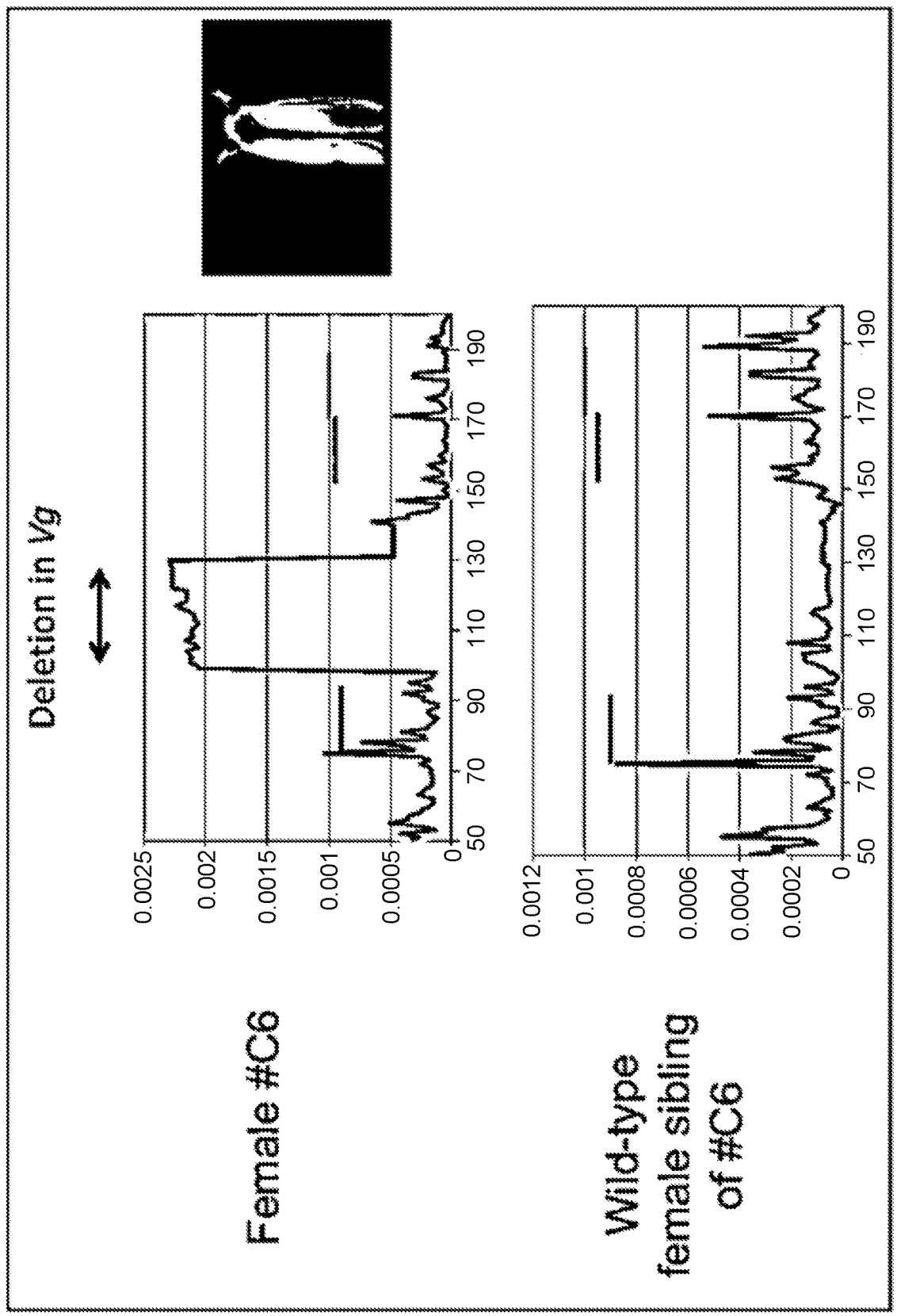
FIG. 11 shows that vestigial mutants have deletions in vg in their genomic DNA.

Injections of Cas9 protein and four vestigial gRNAs produced adult whiteflies with deformed wings at a significantly greater percentage than with injections of gRNAs alone. Increased embryonic lethality was observed when Cas9 was present in the injection mix consistent with both the toxic effects of Cas9 and also with the embryonic lethality associated with many vg mutants (FIGS. 9A and 9B). Molecular analysis of genomic DNA prepared from one adult with a wing deformity revealed deletions between the sites of two vg gRNAs, consistent with the action of the Cas9 endonuclease in the presence of gRNAs (FIGS. 10 and 11).

Figure 13A:
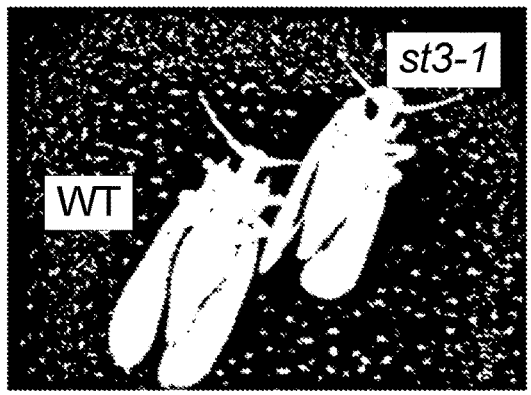
FIGS. 13A and 13B are photographs showing scarlet injection resulted in the appearance of adult whiteflies with bright red eyes.
Figure 13B:
Figure 14:
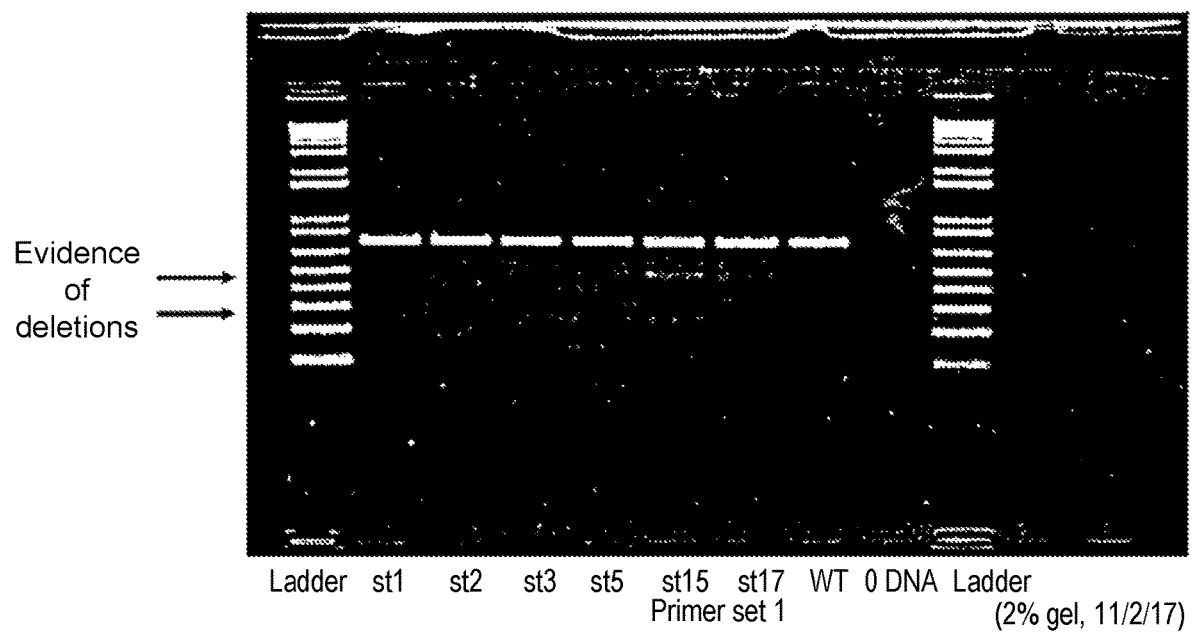
FIG. 14 shows a T7 endonuclease assay demonstrating the mutant adults contain mutations in at least one of the exons targeted by the gRNAs used.

Injections of Cas9 protein and four gRNAs specific to the scarlet gene resulted in the appearance of adult whiteflies with bright red eyes in 9.8% of all adults recovered from these injections (FIGS. 12, 13A, and 13B). Molecular analysis of a selection of these adults revealed they contained mutations in at least one of the exons targeted by the gRNAs used (FIG. 14).

Figure 15B:
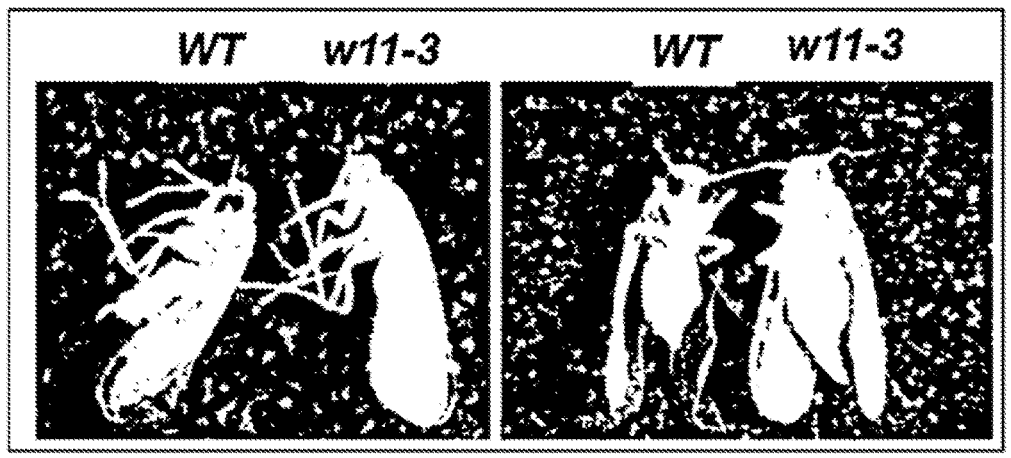
FIG. 15B shows two photographs of two adult male G0 whiteflies, one with wild-type eye color and one with white eye color caused by genome editing mediated by the CRISPR/Cas9 system.

Injections of Cas9 protein with each of four gRNAs specific to the white gene resulted in the appearance of an adult whitefly with white eyes recovered from injections with white gRNA2 (FIGS. 15A and 15B). Molecular analysis of this adult revealed it contained four mutations at or immediate to the PAM site within the gRNA2 target site (FIGS. 16 and 17A). Microinjections with w gRNA2 and Cas9 protein also generated adults with bright red eye color and subsequent molecular analysis of these revealed a mutation at the PAM site within the gRNA2 target site (FIG. 17B).

Example 4: Testing of Phytoagar and Supplements on Leaf Viability to Support Whitefly Nymph Development We determined leaf performance on two media: Murashige & Skoog (MS) and Gamborg's (GB) media. In addition we tested the impact of adding 3% sucrose or Gamborg's vitamins (GBV) as supplements, as well as altering the pH of the media (pH 7.0 vs pH 5.8).

Protocol: Eight media were tested over the course of 10 independent experiments. Murashige & Skoog media, Gamborg's media, and Gamborg's vitamins are purchased from Sigma. The method comprised the following steps: (1) leaf-discs (2.7-cm or 3.0 cm in diameter) were cut from a leaves between 11.5 cm (leaf #2) to 18 cm (leaf #3) in length; (2) six leaf-discs from six-week-old plants were placed on a specific media (see, Table 1 below), covered with a mesh lid, sealed with parafilm, and incubated agar side up; (3) three discs were placed in Incubator A (lower humidity, less intense light) and Incubator B (higher humidity, higher light), plates were covered with fabric screen; (4) discs were assessed daily for leaf-disc growth, disc color, fungal contamination of agar or disc, agar depth (to determine date of transfer) and presence of calli or roots; and (5) discs were transferred to fresh media as needed (usually 7-8 d).

Figure 18A:
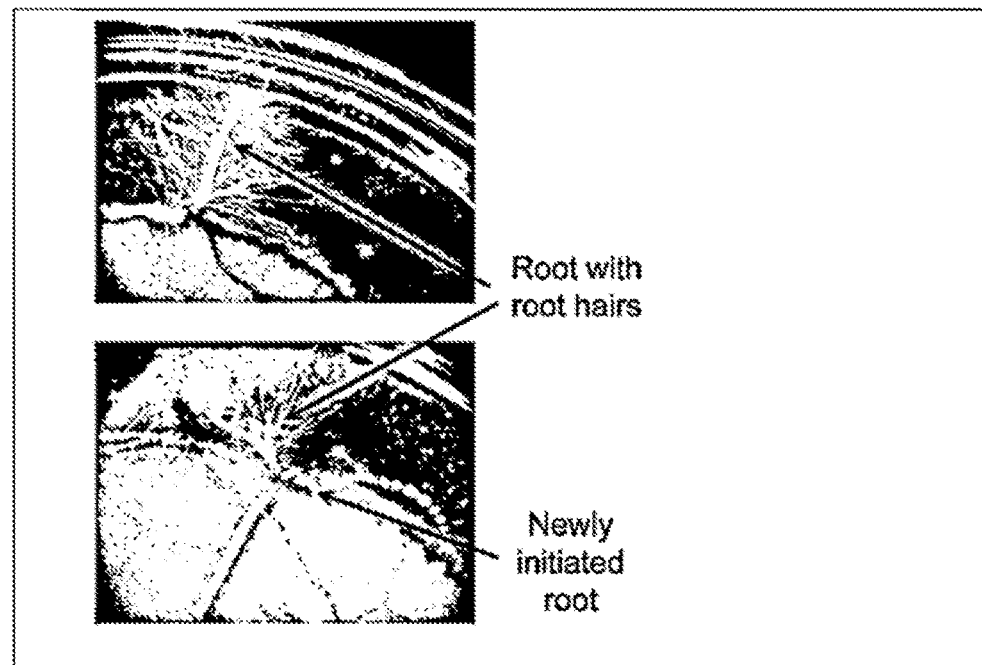
FIG. 18A shows photographs of disc growth on a phytoagar GB+GBV media.

(pH 7.0) (Table 1; FIG. 18A). The lights in incubator B were too intense and extra layers of cloth screens are being used to promote disc health. Light intensity must be monitored in all incubators as light configurations, light intensity and the number of fabric screens influence the amount of light perceived by the discs.

Example 5: The Effect of Phytoagar GB+GBV Media on Plant Disc Size and Viability We determined the optimal disc size from young leaves, as young discs expand rapidly and can exceed dimensions of the plate within a week. We tested the leaf-disc quality of leaf #2 on plants that were 6-, 7- and 9-weeks old. We determined the quality of young (#2), middle aged (#3), and older leaves (#4) from six-week-old plants (see, e.g., FIG. 18B).

Protocol for Age of the plant: Discs were cut from different aged plants (same aged leaf) and from leaves of different ages from the same aged plant. The following steps were performed: (1) leaf-discs (3.0 cm in diameter) were cut from a #2 leaf from plants that were nine-, seven- or six-weeks old; (2) six leaf-discs from each plant were placed on GB+GBV agar plates, covered with a mesh lid, sealed with parafilm, and incubated agar side up; (3) three discs were placed in incubator A (with lower light and lower humidity) and incubator B with (higher light and higher humidity); plates were covered with fabric screen; (4) discs were assessed daily for leaf-disc growth, disc color, fungal contamination of agar or disc, agar depth (to determine date

TABLE 1

MEDIA AND LEAF-DISC PERFORMANCE ASSESSMENT

| EXPT # | MEDIA TESTED | PLANT AGE LEAF # DISC SIZE | CALLI FIRST DAY DETECTED (% PLATES WITH CALLI) | ROOTS FIRST DETECTED |
|---|---|---|---|---|
| 1-3 | 1 -MS<br>2 - MS + GBV pH 5.8<br>3 - MS + GBV pH 7.0 | 6-wk-old<br>Leaf #3<br>3.0-cm disc | 1A - 8 d (17%)<br>1B - 15 d (33%)<br>2A - 8 d (17%)<br>2B - 0%<br>3A - 0%<br>3B - 0% | None |
| 4-6 | 4- GB with sucrose (old media)<br>5- GB + GBV (ph 5.8)<br>6- GB + GBV (ph 7.0) | 6-wk-old<br>Leaf #3<br>3.0-cm disc | 4A - 0%<br>4B - 6 d (17%)<br>5A - 9 d (100%)<br>5B - 6 d (33%)<br>6A - 10 d (67%)<br>6B - 6 d (17%) | 4A - 0%<br>4B - 0%<br>5A - 11 d<br>5B - 9 d (33%); 10 d 67%)<br>6A - 11 d (100%)<br>6B - 9 d (67%); 10 d (100%) |
| 16-17 | 16- GB<br>17-GB + GBV | 5.5 weeks<br>Leaf 2 | 16A - 6 d (100%)<br>16B - 4 d (33%); 5 d (100%)<br>17A - 5 d (67%) 7 d (100%)<br>17B - 5 d (33%)<br>6 d (67%)<br>8 d (100%) | 16A - 5 d (33%);<br>10 d (100%)<br>16B - 8 d (33%)<br>17A - 6 d (33%)<br>10 d (67%)<br>17B - 10 d (33%)<br>15 d (67%) |
| 22-23 | 22AB- GB (pH 7.0)<br>23AB- GB + GBV (pH 7.0) | 6 weeks<br>Leaf 2 | 22A-4 d (33%)<br>5 d (100%)<br>22B-5 d (100%)<br>23A-5 d (33%)<br>9 d (100%)<br>23B-5 d (100%) | 22A- 8 d (33%)<br>22B- 7 d (67%)<br>8 d (100%)<br>23A-9 d (67%)<br>10 d (100%)<br>23B-7 d (33%)<br>9 d (100%) |

Conclusions: While all media supported leaf viability, Gamborg's vitamins (GB+GBV) performed optimally (Table 1). Surprisingly, discs on GB+GBV promoted the formation of adventitious roots (see FIG. 18A). GB+GBV (pH 5.8) produces roots a few days earlier than GB+GBV of transfer) and presence of calli or roots; and (5) discs were transferred to fresh media as needed (usually at 7-8 d).

Protocol for Age of the leaf: The following steps were performed: (1) nine leaf-discs (2.5-cm or 3.0 cm in diameter) were cut from a 6-week-old plants; (2) six leaf-discs were cut from leaf 2 (11.5-cm long), leaf 3 (18-cm long) and leaf 4 (24-cm long) (see, e.g., FIG. 18B); (3) discs were placed on GB+GBV agar plates, covered with a mesh lid, sealed with parafilm, and incubated agar side up; (4) Three discs were placed in Incubator A (lower light and lower humidity) and Incubator B (higher light and higher humidity); plates were covered with fabric screen; (5) discs were assessed daily for leaf-disc growth, disc color, fungal contamination of agar or disc, agar depth (to determine date of transfer) and presence of calli or roots; and (6) discs were transferred to fresh media as needed (usually 7-8 d).

Protocol for Disc size: The method comprised the following steps: (1) six leaf-discs 2.5-cm in diameter and six leaf-discs 3.0-cm in diameter were cut from a 6-wk-old plants were cut from leaf 2 (11.5-cm long.); (2) discs were placed on GB+GBV agar plates, covered with a mesh lid, sealed with parafilm, and incubated agar side up; and (3) three discs from each experiment were placed in incubator B (higher light and higher humidity). Plates were covered with one fabric screen; (4) discs were assessed daily for leaf-disc growth, disc color, fungal contamination of agar or disc, agar depth (to determine date of transfer) and presence of calli or roots; and (5) discs were transferred to fresh media as needed (usually 7-8 d).

TABLE 2

PLANT AGE-LEAF-DISC PERFORMANCE ASSESSMENT

| Expt # | Parameter tested | Leaf # disc size | Leaf-disc health | Calli first day detected (% plates with calli) | Roots first detected |
|---|---|---|---|---|---|
| 26B | 9-wk-old plant | Leaf 3 3.0-cm disc | 26B - GP (10 d) | 5 d - 33% 7 d- 67% 10 d- 100% | 20d - 0% |
| 27B | 7-wk-old plant | Leaf 3 3.0-cm disc | 27B - GY (12 d) GP (13 d) | 4 d - 67% 7 d - 100% | 8d - 33% |
| 28B | 6-wk-old plant | Leaf 3 3.0-cm disc | 28B - GP (12 d) | 4 d - 67% 5 d - 100% | 8d - 33% 9d - 100% |
| 33A | 6-wk-old plant | Leaf 2 2.5-cm | 33A-G (15 d) | 33A- 5 d -67% 7 d - 100% | 33A- 10 d 33% |
| 33B | 6-wk-old plant | Leaf 2 2.5-cm | 33B-GP (9 d) | 33B-4 d -67% 6 d - 100% | 33B- 8 d- 33% 9 d - 67% |
| 34A | 7-wk-old plant | Leaf 2 2.5-cm | 333A-G (15 d) | 34A-6 d - 100% | 34A- 15 d 0% |
| 34B | 7-wk-old plant | Leaf 2 2.5-cm | 33B-GP (9 d) | 34B-7 d-33% 9 d-100% | 34B-15 d 0% |

TABLE 3

LEAF AGE-LEAF-DISC PERFORMANCE ASSESSMENT

| Expt # | Parameter tested | Leaf # disc size | Leaf-disc health | Calli first day detected (% Plates with calli) | Roots first detected |
|---|---|---|---|---|---|
| 7AB | Leaf 2 6-wk-old plant | 6-wk-old plant 2.5-cm disc | 7A - G to end 7B - GP (10 d) | 8 d - 100% 8 d-100% | 11 d - 0% 15 d - 0% |
| 8AB | Leaf 3 6-wk-old plant | 6-wk-old plant 2.5-cm disc | 8A - G to end 8B - GP (10 d) | 8 d - 67% 9 d - 100% 8 d -67% | 15 d - 0% 23 d - 30% |
| 9AB | Leaf 4 6-wk-old plant | 6-wk-old plant 3.0-cm disc | 9A - G to end 9B - GP (10 d) | 8 d - 0% 8 d - 0% | 8 d - 0% 8 d - 0% |

TABLE 4

LEAF-DISC SIZE OPTIMIZATION

| Expt # | Parameter tested | Leaf # disc size | Leaf-disc health | Calli first day detected (% Plates with calli) | Roots first detected |
|---|---|---|---|---|---|
| 14B | Leaf 2 6-wk-old plant | 6-wk-old plant 2.5-cm disc | 14B - GP (8 d) Approx 3.0 cm in 9 d | 5 d - 67% 8 d-100% | 8 d - 0% 8 d - 0% |
| 15B | Leaf 2 | 6-wk-old plant | 15B - GP (7 d) | 8 d - 100% | 9 d - 0% |

Figure 18B:
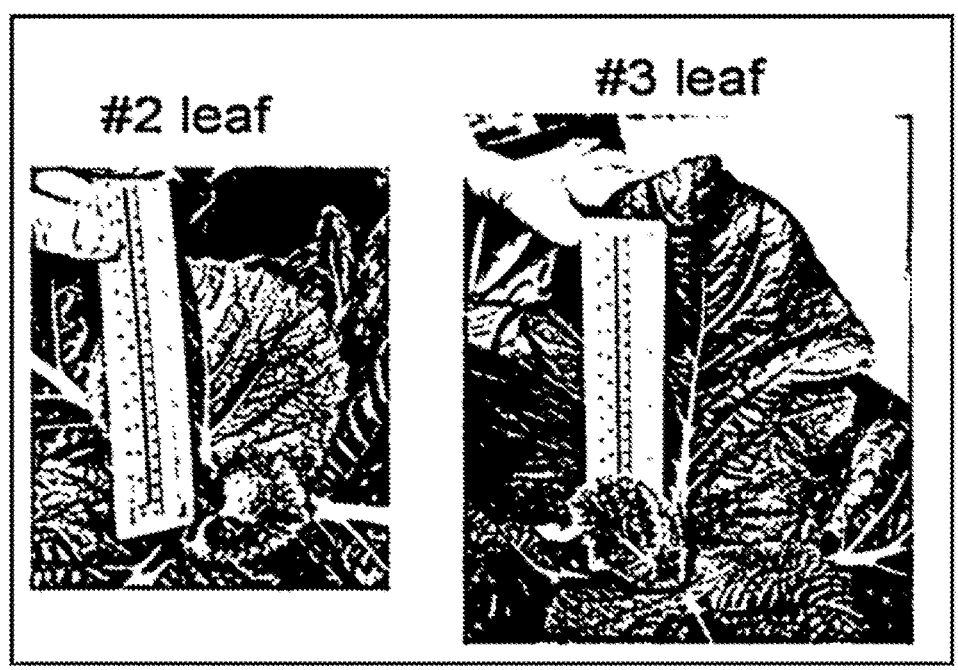
FIG. 18B shows photographs demonstrating the sizes of leaf 2 and leaf 3 from *Brassica* plants.

Conclusions: We found that the leaf-discs from nine-week-old plants senesce early (within 2 weeks) in the leaf-disc system. We also found that leaf-discs from seven- and six-week-old plants stayed green for the duration of the experiment (4 weeks). Younger leaves (11.5 cm, leaf 2) and (18 cm, leaf 3) lived longer in the leaf-disc system than an older leaf (>24 cm, leaf 4). Discs from leaf 2 and 3 expanded rapidly and 3.0-cm discs exceeded the surface area of the agar plate within 9 d (FIG. 18B). Lastly, we found 2.5-cm diameter discs are optimal for this system.

Example 6: To Determine if Rooted-Discs in the Leaf-Disc System Enhance Whitefly Rearing This experiment was conducted to determine if leaf-discs with roots are advantageous to leaf-disc health, and in turn, advantageous whitefly nymph rearing and development.

Overview: We have determined that young *Brassica* leaf-discs form roots. Rooted leaf-discs have increased longevity and vitality. We have shown that whiteflies usually inhibit root initiation and growth. Therefore, to harness rooted discs in the leaf-disc system, we must pretreat leaf-discs to enhance root growth. Preliminary experiments and discoveries indicate that these pretreatments will enhance whitefly rearing. A schematic for our pre-treatment protocol is shown in FIG. 19.

Protocol: To Enhance Root Growth The method comprised the following steps: Leaf-discs (2.5-cm or 3.0-cm in diameter) from a 6-wk-old plants were cut from leaf 2 (11.5-cm long); (2) discs were placed on GB+GBV agar plates, covered with a mesh lid, sealed with parafilm, and incubated agar side up; (3) in some experiments, GB+GBV plates were initially incubated agar side down to encourage root growth into the media. The plates were then flipped and incubated agar side up for the remainder of the experiment; (4) three discs from each experiment were placed in Incubator B (higher light and higher humidity). Plates were covered with two fabric screens. Three discs from each experiment were placed in Incubator A (lower light and lower humidity). Plates were covered with one fabric screen; (5) discs were assessed daily for leaf-disc growth, disc color, fungal contamination of agar or disc, agar depth (to determine date of transfer) and presence of calli or roots; (6) discs are transferred to fresh media as needed (usually 7-8 d); and (7) when significant root networks were formed, they were transferred the leaf-disc with its root system and agar into "halo" plates using a small spatula (see, Halo Plate protocol below) (schematic shown in FIG. 19).

Protocol: Halo plates 6.0 and 10-cm: The method comprised the following steps: In the center of the larger plates, we placed a 3.5-cm petri dish with weights (so it does not float when agar is poured around it. Then, GB+GBV agar is poured around the 3.5-cm dish to make a ring (a halo) of GB+GBV agar. Once the agar was solidified, the 3.5-cm plate is removed. The leaf-disc, root system and agar in the 3.5-cm plate is transferred to the plate with the agar ring. Cooled, almost solidified, GB+GBV agar was gently pipetted into the space to seal the ring of agar with the transferred leaf-disc. Care was taken not to get agar on the leaf surface.

Conclusions: Leaf-discs from six-week-old plants on GB+GBV media can produce roots with varying efficiencies (33%-100%) often in 9-10 d. Younger leaves (11.5 cm, leaf 2) and (18 cm, leaf 3) produce roots on GB+GBV (Expt.5AB, 6AB, 17AB, 8B, etc). Disc with roots usually remain green, continue to expand and become more turgid that discs without roots (FIGS. 20A and 20B). Life spans (without whitefly infestation) have been as long as 2 months. Disc with roots that are beginning to yellow or have produced anthocyanins (a sign of stress) often regreen and become more turgid that discs without roots. We can transfer the leaf-disc with its root system to larger "halo" plates (either 6.5-cm or deep 10-cm diameter plates) that allow the development of robust root systems with 100% efficiency (FIGS. 21A and 21B). Whiteflies tend to suppress root development; although rare exceptions do occur. Roots are gravitropic. Therefore, in our leaf-disc system where the agar side of the plate is up and whiteflies are below (see, FIGS. 21A and 21B), roots grow out of agar and are aerial. If we incubate discs on GB+GBV plates for several days with agar side down, roots initiate and grow into the agar. At this time, roots are primarily within the agar and form a robust root system. Discs on halo plates often to not make good contact with agar; sometimes they are solely anchored by their roots (Expt. 5B, 6B, 8B) (FIGS. 21A and 21B). Whitefly eggs on discs transferred to halo plates can be injected and nymphs emerge (Expt. 8B).

Example 7: Surface Sterilization of Leaf-Discs with Ethanol and Sodium Hypochlorite To determine if surface sterilization of leaf-discs with EtOH (i.e., ethanol) and sodium hypochlorite will control fungi that commonly contaminate leaf-discs and the surface of GB+GBV phytoagar plates.

Fungi that are resident on leaf surfaces will populate the agar, edges of leaf-discs and when inadvertent leaf damage occurs sites of damage. Fungi on the leaf-disc are likely to induce plant defenses making the disc a non-optimal environment for rearing whiteflies. Standard methods for surface sterilization of leaves were explored to eliminate or minimize plant-derived fungi.

Protocol 1: Ethanol and sodium hypochlorite: The method comprised the following steps: (1) whole leaves (Leaf 2 or leaf 3) were excised from plants; (2) leaves were dipped in 500 ml of 70% EtOH for 10-20 sec; (3) leaves were immersed in 500 ml of 0.01%, 0.06% or 0.24% NaClO for varying periods of time (1-20 min) with and without agitation of the liquid; (4) leaves were washed three to four times in distilled water (500-ml) each; (5) leaves were patted dry with paper towels; and (6) discs are cut from these pretreated leaves. Optionally, one may proceed by continuing on to step 6, in Protocol 2 as outlined below.

Protocol 2: Ethanol and sodium hypochlorite: The method comprised the following steps: (1) leaf-discs (2.5-cm in diameter) were cut from leaf 2 (11.5-cm long) or leaf 3 from a 6-wk-old plants; (2) Discs were dipped in 500 ml of 70% EtOH for 10-20 sec; (3) Discs were immersed in 500 ml of 0.01%, 0.06% or 0.24% NaClO for varying periods of time (1-20 min) with and without agitation of the liquid; (4) Discs were washed three to four times in distilled water (500-ml) each; (5) Discs were patted dry with paper towels; (6) Discs were placed on GB+GBV agar plates, covered with a mesh lid, sealed with parafilm, and incubated agar side up; (7) In some experiments, GB-GBV plates were initially incubated agar side down to encourage root growth into the media. The plates were then flipped and incubated agar side up for the remainder of the experiment; (8) three discs from each experiment were placed in Incubator B (higher light and higher humidity). Plates were covered with two fabric screens. Three discs from each experiment were placed in Incubator A (lower light and lower humidity). Plates were covered with one fabric screen. In most experiments both incubators were used; and (9) discs were assessed daily for leaf-disc growth, disc color, fungal contamination of agar or disc, agar depth (to determine date of transfer) and presence of calli or roots; (10) Discs were transferred to fresh media as needed (usually 7-8 d).

Conclusions: Plant-derived fungi develop on GB+GBV phytoagar plates within 3-4 d. Prewashing leaves or leaf-discs with 70% EtOH and 0.01% NaClO (or 0.06% NaClO) slows the timing of first appearance of fungi on agar plates by 1-2 days. This does not adequately plant-leaf resident fungi. No damage was evident to intact leaves or leaf-discs (Expt. 66-71B, Expt. 37-39B). Prewashing intact leaves with 70% EtOH and 0.24% NaClO and then cutting discs prevents the appearance of fungi for 19 days (Expt. 22AB-25AB).

Example 8: Surface Sterilization of Leaf-Discs with DMSO and Miconazole

The long-term goal is to determine if fungicides can be used to control the whitefly-introduced fungi in the leaf-disc system.

Whiteflies that are introduced into leaf-disc system are collected from colonies with aged *Brassica* plants that are often infected with fungi. Fungi are supported in the colonies due to the whitefly honeydew (high sugar content excrement) that falls onto leaves. Plants cannot be treated with fungicides to control fungal infections due to insectary policies and potential harm to the whiteflies and its microbial endosymbionts. A mechanism to control the fungi introduced on whitefly feet and bodies must be developed.

The first step is to determine if the solvent for many fungicides (DMSO) can be tolerated by leaf-discs.

Protocol: DMSO Spray (Expt. 56-58AB): The method comprised the following steps: (1) leaf-discs (2.5-cm in diameter) were cut from a 6-wk-old plants were cut from leaf 2 (11.5-cm long) or leaf 3. There was no surface sterilization pretreatment; (2) discs were placed on GB+GBV agar plates; (3) disc were sprayed using a Preval Atomizer with 20% DMSO or water (control); (4) some plates were allowed to dry overnight in the hood. Other plates covered with a mesh lid, sealed with parafilm, and incubated agar side up; (5) three discs from each experiment were placed in Incubator B (higher light and higher humidity). Plates were covered with two fabric screens. Three discs from each experiment were placed in Incubator A (lower light and lower humidity). Plates were covered with one fabric screen. In most experiments both incubators A and B were used; (6) discs were assessed daily for leaf-disc growth, disc color, fungal contamination of agar or disc, agar depth (to determine date of transfer) and presence of calli or roots. In the DMSO experiments, evidence of water soaked lesions and DMSO puddles that had not been absorbed by the leaf were noted; and (7) discs were transferred to fresh media as needed (usually 7-8 d).

Protocol: DMSO and DMSO/miconazole dips (Expt. 47-49AB): The method comprised the following steps: (1) leaf-discs (2.5-cm in diameter) were cut from leaf 2 (11.5-cm long) or leaf 3 from a 6-wk-old. There was no surface sterilization pretreatment; (2) discs were dipped several times in 20% DMSO, 8% DMSO or water (control). Discs were allowed to dry for a short time in the hood. Any residual bubbles of DMSO were removed from the disc surface with a Q-tip; (3) discs were placed on GB+GBV agar plates, covered with a mesh lid, sealed with parafilm, and incubated agar side up; (4) three discs from each experiment were placed in Incubator B (higher light and higher humidity). Plates were covered with two fabric screens. Three discs from each experiment were placed in Incubator A (lower light and lower humidity). Plates were covered with one fabric screen. In most experiments both incubators were used; (5) discs were assessed daily for leaf-disc growth, disc color, fungal contamination of agar or disc, agar depth (to determine date of transfer) and presence of calli or roots. Few water soaked lesions and DMSO puddles with the dip method were observed; and (6) discs were transferred to fresh media as needed (usually 7-8 d).

Conclusions: Direct spraying of leaf-disc with 20% DMSO using two different types of atomizers causes extensive damage to leaf-discs. Pools of DMSO cause water-soaked lesions, which are readily infested by resident fungi. (Expt. 56-58AB). Dipping leaf-discs into 8% or 20% DMSO does not cause leaf-disc damage. This will be the pretreatment application mode to control fungi. (Expt. 37-39B; 66-71B). Dipping of leaf-discs in 8% DMSO and 5 µg/ml miconazole slows the growth of plant-derived fungi by 10-12 d.

Example 9: Eggplant as an Alternative Host for Whitefly Rearing

Protocol: The method comprised the following steps: (1) leaf-discs (2.5-cm in diameter) were cut from eggplant leaves (approx . . . 8-weeks old), (2) discs were placed on GB+GBV agar plates, covered with a mesh lid, scaled with parafilm, and incubated agar side up. Some discs on GB+GBV plates were subsequently infested with whiteflies for 1-2 d. Adults were removed and nymphs were allowed to develop. Discs from each experiment were placed in Incubator B (higher light and higher humidity). Plates were covered with two fabric screens. Additional discs from each experiment were placed in Incubator A (lower light and lower humidity). Plates were covered with one fabric screen. Discs were assessed daily for leaf-disc growth, disc color, fungal contamination of agar or disc, agar depth (to determine date of transfer) and presence of calli or roots. For whitefly-infested discs, time of emergence of first, 2nd, 3rd, 4th instars, psuedopupae (with red eyes), and adults were noted. Discs were transferred to fresh media as needed (usually 7-8 d).

Conclusions: Eggplant leaf-discs can be used in the leaf-disc system with GB+GBV media. Eggplant discs make exceptionally strong contact with agar leaving a deeper imprint of the leaf surface than do *Brassica* leaf-discs (FIG. 22). Eggplant discs become very turgid in the leaf-disc system and transfer to new agar is sometimes problematic since poor contact with the new agar plate often occurs. However, even limited points of contact allow the eggplant discs to persist for the sufficient length of time to raise whiteflies. Eggplant leaf blades (from which discs are cut) have teeth that adhere to the agar and cause GB+GBV agar to crack. Eggplant discs expand rapidly on GB+GBV plates and smaller initial disc sizes may need to be considered. Whiteflies develop 2-3 days earlier on eggplant discs (Expt. 43-44), which could be advantageous in terms of whitefly rearing. This may provide up to an additional two generations of breeding per year.

Example 10: Injections and Rearing Methods for the Glassy-Winged Sharpshooter (*Homalodisca vitripennis*)

Protocol: The Glassy-winged sharpshooter was reared and injected using the methods provided above.

Conclusion: The Glassy-winged sharpshooter (GWSS) lay or oviposit eggs side-by-side in a slightly curved 'blister-like' raft below the epidermis of plant leaves. GWSS egg rafts were excised from sorghum leaves and placed on GB+GBV plates (FIG. 23). Eggs were successfully injected and survivorship (emergence of nymphs) was typically 50-75%. GWSS nymphs emerge almost synchronously within a 1-3 day window.

Example 11: Phytoagar Media (Minerals, Vitamins, and pH) for Eggplant Leaf-Disc Viability Purpose: Determine the optimal phytoagar for eggplant leaf-disc viability. Healthy leaves provide a growth environment that will support whitefly nymph development. Whiteflies develop 2-3 days earlier on eggplant discs, which could be advantageous in terms of whitefly rearing. This may provide up to an additional two generations of breeding per year.

Overview: We determined leaf performance on two media: Murashige & Skoog (MS) and Gamborg's (GB) media. In addition, we tested the impact of adding 3% sucrose or Gamborg's vitamins (GBV) as supplements, as well as altering the pH of the media (pH 7.0 vs pH 5.8).

Protocol: Eight media were tested over the course of 10 independent experiments. Murashige & Skoog media, Gamborg's media, and Gamborg's vitamins were purchased from Sigma. The general method appears below.

1. Leaf-discs (2.7-cm in diameter) were cut from a leaves (7.5-7.8 inches long and 5-6 inches wide) of young eggplants.

2. Three leaf-discs from six-week-old plants were placed on a specific media (see Table 5), covered with a mesh lid, sealed with parafilm, and incubated agar side up.
3. The discs were placed in Incubator B (higher humidity, higher light). Plates were covered with two fabric screens.
4. Discs were assessed daily for leaf-disc growth, disc color, fungal contamination of agar or disc, agar depth (to determine date of transfer), and presence of calli or roots.
5. Discs were transferred to fresh media as needed (usually 7-8 d). Upon transfer, we found that eggplant discs were very turgid and contact with media surface after transfer was not 100%; despite this disc continued to be healthy and turgid.

TABLE 5

EGGPLANT DISCS AND PHYTOAGAR MEDIA

| Expt # | Media tested | Calli first day detected (% plates with calli) | Roots first detected |
|---|---|---|---|
| 106 | MS | 3 d (33%) 5d (67%) | None |
| 107 | MS + GBV pH 5.8 | 3 d (67%) 5d (100%) | |
| 108 | MS pH 7.0 | 3 d (67%) 5 d (100%) | 12 d (33%) |
| 109 | MS + GBV pH 7.0 | 3 d (33%) 4 d (100%) | |
| 110 | GB | 3 d (67%) 5 d (100%) | 11 d (33%) |
| 111 | GB + GBV | 3 d (67%) 5 d (100%) | 12 d (33%) |
| 112 | GB pH 7.0 | 3 d (67%) | |
| 113 | GB + GBV pH 7.0 | 3 d (67%) 5 d (100%) | |

Conclusion: All media supported eggplant leaf viability. As Gamborg's vitamins (GB+GBV) performs optimally for *Brassica*, we chose GB+GBV as the standard media. Relative to *Brassica*, eggplant rarely produced roots in culture. Earliest root emergence was 11 days after transfer to media. Roots often emerged from calli. This contrasts to *Brassica* where roots emerge independent of calli.

Example 12: Harness Roots to Increase Leaf-Disc Longevity

Purpose: To determine if phytohormone treatments would accelerate production of roots from leaf-discs to improve leaf-disc health and, thereby, whitefly nymph development.

Overview: We have previously determined that young *Brassica* leaf-discs form roots in 9-10 d on GB+GBV media in a high humidity growth chamber (>84% humidity). Rooted discs have increased longevity and vitality. We have shown that whiteflies usually inhibit root initiation and growth; therefore, to harness rooted discs in the leaf-disc system, we must pretreat leaf-discs to enhance root growth.

Protocol

1. Leaf-discs (2.7-cm in diameter) were cut from *Brassica* leaves (Leaf #2, leaf #3) or eggplant leaves (see above).
2. Three leaf-discs were placed on a specific media (see Tables 6 and 7 below), covered with a mesh lid, sealed with parafilm, and incubated agar side up.
3. The discs were placed in Incubator B (higher humidity, higher light). Plates were covered with two fabric screens.
4. Discs were assessed daily for leaf-disc growth, disc color, fungal contamination of agar or disc, agar depth (to determine date of transfer), and presence of calli or roots (number of root sites and number of roots/site).
5. Discs were transferred to fresh media as needed (usually 7-8 d).

TABLE 6

*BRASSICA* AND IBA

| Expt # | Media tested | Calli first day detected (% plates with calli) | Roots first detected |
|---|---|---|---|
| 128 | GB + GBV | 4 d (67%) 5 d (67%) | |
| 129 | GB + GBV (2.5 mg/L IBA) | 4 d (100%) | 5 d 129B-3 1 site/1 root 6d 129B-1 4 sites 129B-2 3 sites 129B-3 4 sites |
| 130 | GB + GBV (5 mg/L IBA) | 4 d (67%) 5 d (100%) | 5 d 130B-2 2 sites/ 3-4 roots per site 6 d 130B-1 3sites/ 2 roots per site 130B-2 >3 sites/ 6 roots per site 130B-3 6 sites |
| 131 | GB + GBV (7.5 mg/L IBA) | 4 d (100%) | 6 d 131B-2 2 sites/ 2-3 per site 131B-3 3 sites/ multiple per site |
| 132 | GB + GBV (10 mg/L IBA) | 4 d (100%) | 5 d 132B-1 9 sites/ 1-4 roots per site 5 d 132B-3 4 sites/ 1 root per site 6d 132B-1 over 41 roots total 132B-2 10 sites 132B-3 15 sites |

TABLE 7

*BRASSICA* AND NAA (NAPTHALENE ACETIC ACID)

| Expt # | Media tested | Calli first day detected (% plates with calli) | Roots first detected |
|---|---|---|---|
| 139 | GB + GBV | 4 d (67%) 5 d (67%) | |
| 140 | GB + GBV (0.1 mg/L NAA) | 4 d (33%) 5 d (100%) | 5 d 140B-1 1 site/1 root 140B-3 1 site/1 root |
| 141 | GB + GBV (1 mg/L NAA) | 4 d (67%) 5 d (67%) | 4 d 141B-1 3 sites/ 1-3 roots per site 141B-2 1 sites/ 1 roots per site 141B-3 2 sites/ 1-2 roots per site 5 d 141B-1 4 sites/ 1-3 roots per site 141B-2 2 sites/ 1-2 roots per site |
| 141 | GB + GBV (10 mg/L NAA) | 3 d (100%) | 141B-3 2 sites/ 1-2 roots per site 4 d 142B-1 1 sites/ 2 per site 142B-2 3 sites/ 1-3multiple per site 142B-3 1 sites/ 5 per site 5 d 142B-1 1 sites/ 2 per site |

TABLE 7-continued

BRASSICA AND NAA (NAPTHALENE ACETIC ACID)

| Expt # | Media tested | Calli first day detected (% plates with calli) | Roots first detected |
|---|---|---|---|
| | | | 142B-2 6 sites/ 1-3multiple per site |
| | | | 142B-3 3 sites/ 1-3 per site |

Conclusion: Indole Butyric Acid Stimulates and Accelerates Root Production in *Brassica* Discs GB+GBV with IBA at six different concentrations were tested: 0 (control), 0.1, 1.0, 2.5, 5.0, 7.5 and 10 mg/L). see Table 6. Indole butyric acid (IBA) enhanced and accelerated the production of roots from *Brassica* leaf-discs. Leaf-discs produced roots in 5-6 days on GB+GBV supplemented with IBA. Concentrations producing roots reproducibly ranged from 2.5 mg/L to 10 mg/L. Roots were occasionally detected in 1.0 mg/L IBA. Experiments indicated that 1 day on 10 mg'L IBA plates may be sufficient to accelerate root production.

Indole Butyric Acid does not Significantly Impact Root Production in Eggplant Discs GB+GBV with IBA at three different concentrations were tested: 0 (control), 0.1, 1.0, and 10 mg/L). IBA did not significantly enhance or accelerate root production in eggplant. Only one disc (GB+GBV+10 mg/L. IBA) formed roots after 10 d. Calli were formed with 5 days on all media. Roots emerged from calli.

Napthalene Acetic Acid (NAA) Stimulates and Accelerates Root Production in *Brassica* Discs GB+GBV with NAA at three different concentrations were tested: 0 (control), 0.1, 1.0, and 10 mg/L). see Table 7. NAA (0.1, 1.0 and 10 mg/L) enhanced and accelerated the production of roots from *Brassica* leaf-discs. Multiple root sites and multiple roots per site were detected at these NAA concentrations. Roots were first detected on all three plates with NAA 1 mg/L or 10 mg/L by day 4. o Roots were detected on ⅔ plates with NAA 0.1 mg/L on day 5. Multiple roots sites per disc and multiple roots per site were detected on all plates.

Napthalene Acetic Acid does not Significantly Impact Root Production in Eggplant Discs GB+GBV with NAA at three different concentrations were tested: 0 (control), 0.1, 1.0, and 10 mg/L). NAA (0.1, 1.0 and 10 mg/L) did not produce of roots from eggplant leaf-discs within 5 d.

One or more features from any embodiments described herein or in the figures may be combined with one or more features of any other embodiment described herein in the figures without departing from the scope of the invention.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An assay system for testing the effect of a chemical on an insect comprising:
   a rooted leaf-disc;
   an agar; and
   a solution comprising Gamborg's (GB) media supplemented with Gamborg's vitamins (GBV).

2. The assay system of claim 1, further comprising a phytohormone.

3. The assay system of claim 1, further comprising a solution for surface sterilization.

4. The assay system of claim 1, further comprising a chemical, wherein the chemical is supplied by the user and is a pesticide, an insecticide, or a pheromone.

5. The assay system of claim 1, wherein the leaf-disc comprises a *Brassica*, a citrus leaf, a tomato leaf, or an eggplant leaf.

* * * * *